United States Patent
Stehr et al.

(10) Patent No.: US 9,890,415 B2
(45) Date of Patent: Feb. 13, 2018

(54) METHOD FOR DETECTING A NUCLEIC ACID

(71) Applicant: GNA Biosolutions GmbH, Planegg/Martinsried (DE)

(72) Inventors: Joachim Stehr, München (DE); Federico Bürsgens, München (DE); Lars Ullerich, München (DE); Lidiya Osinkina, München (DE); Cecilia Rebuffo-Scheer, München (DE)

(73) Assignee: GNA Biosolutions GmbH, Planegg/Martinsried (DE)

( * ) Notice: Subject to any disclaimer, the term of this patent is extended or adjusted under 35 U.S.C. 154(b) by 0 days.

(21) Appl. No.: 15/216,342

(22) Filed: Jul. 21, 2016

(65) Prior Publication Data

US 2017/0037454 A1 Feb. 9, 2017

(30) Foreign Application Priority Data

Aug. 3, 2015 (DE) .......... 10 2015 010 069

(51) Int. Cl.
*G01N 21/64* (2006.01)
*C12Q 1/68* (2018.01)

(52) U.S. Cl.
CPC .......... *C12Q 1/6818* (2013.01); *C12Q 1/686* (2013.01); *C12Q 1/6816* (2013.01)

(58) Field of Classification Search
CPC ......... C12Q 1/68; C12M 1/34; G01N 33/587; G01N 21/64; G01N 27/127; G01N 33/54346; C07H 21/04; C40B 30/04

See application file for complete search history.

(56) References Cited

U.S. PATENT DOCUMENTS 6,361,944 B1 * 3/2002 Mirkin ................ C12Q 1/6837
435/6.11
7,179,658 B2 * 2/2007 Cheng ................ C12Q 1/6818
204/451

(Continued)

FOREIGN PATENT DOCUMENTS

| WO | 2009149091 A1 | 12/2009 |
| WO | 11/160887 A1 | 12/2011 |
| WO | 2014065753 A1 | 5/2014 |

OTHER PUBLICATIONS

Song et al, A facile fluorescencemethodforversatilebiomoleculardetection based onpristine α-Fe2O3 nanoparticle-induced fluorescence quenching, 2015, Biosensors and Bioelectronics 68, 239-244.*

(Continued)

*Primary Examiner* — Narayan Bhat
(74) *Attorney, Agent, or Firm* — Lathrop Gage LLP

(57) ABSTRACT

A method for detecting at least one nucleic acid in a solution, comprising the steps of: providing at least one dye, wherein the solution and/or a reaction vessel, wherein the solution is present, comprises the dye and wherein the at least one dye is adapted to emit emission light due to an optical excitation by excitation light; providing at least one absorber in the solution, wherein the absorber is adapted to cause an attenuation of the emission light and/or the excitation light and wherein the attenuation is influenced by a bonding of the at least one absorber to the nucleic acid; and radiating excitation light into the solution and measuring an intensity of the emission light; wherein the attenuation of the emission light and/or the excitation light by the at least one absorber occurs independently of a quantum yield of the at least one dye.

21 Claims, 7 Drawing Sheets

(56) References Cited

U.S. PATENT DOCUMENTS

| | | | |
|---|---|---|---|
| 2003/0059850 A1 | 3/2003 | Evans | |
| 2010/0075335 A1 | 3/2010 | Ramos | |
| 2013/0085078 A1* | 4/2013 | Schrader | C12Q 1/6818 506/9 |
| 2015/0017258 A1 | 1/2015 | Azzazy | |

OTHER PUBLICATIONS

Song et al, A facile fluorescencemethodforversatilebiomoleculardetection based onpristine α-Fe2O3 nanoparticle-induced fluorescence quenching, 2015, Biosensors and Bioelectronics 68, 239-244, Supplemental information, pp. 1-7.*
Wurth et al, Relative and absolute determination of fluorescence quantum yields of transparent samples, 2013, Nature Protocols, 8, 1535-1550.*
Agasti et al., "Nanoparticles for Detection and Diagnosis"; Adv. Drug Deliv. Rev., 62(3):316-328 (2010).
International Search Report and Written Opinion for corresponding PCT application No. PCT/EP2016/001259, dated Nov. 3, 2016.
Wang et al., "Gold Nanoparticle-Based Colorimetric and "Turn-on" Fluorescent Probe for Mercury(II) Ions in Aqueous Solution", Analytical Chemistry, 80(23):9021-9028 (2008).
Gill et al., "Fast, single-step, and surfactant-free oligonucleotide modification of gold nanoparticles using DNA with a positively charged tail", ChemCom., 49(97):11400-11402 (2013).
Kanjanawarut et al., "Colorimetric Detection of DNA Using unmodified Metallic Nanoparticles and Peptide Nucleic Acid Probes", Analytical Chemistry, 81(15):6124-6125 (2009).

* cited by examiner

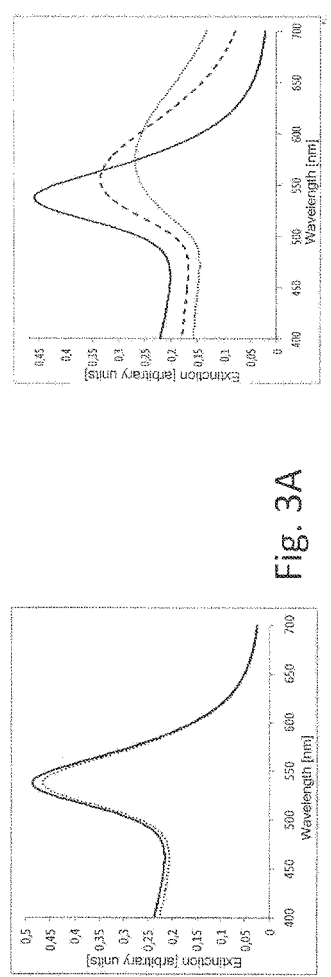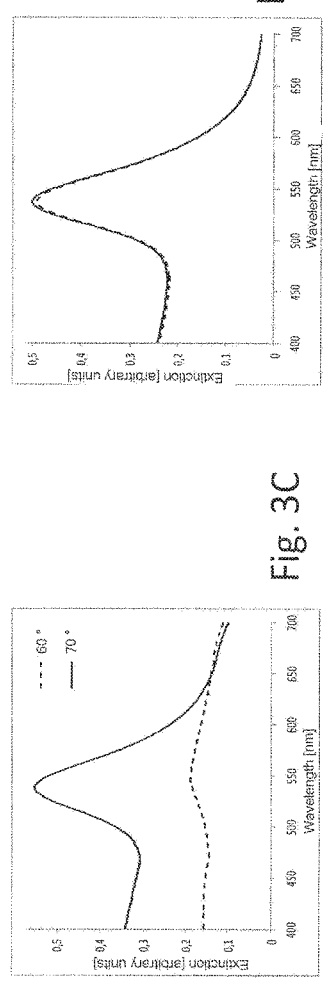
Fig. 3A
Fig. 3B
Fig. 3C
Fig. 3D

METHOD FOR DETECTING A NUCLEIC ACID

The invention relates to a method for detecting at least one nucleic acid to be detected in a solution, comprising the steps of:
providing at least one dye, wherein the solution and/or a reaction vessel, wherein the solution is present, comprises the dye and wherein the at least one dye is adapted to emit emission light due to an optical excitation by excitation light;
providing at least one absorber in the solution, wherein the absorber is adapted to cause an attenuation of the emission light and/or the excitation light and wherein the attenuation is influenced by a bonding of the at least one absorber to the nucleic acid to be detected; and
radiating excitation light into the solution and measuring an intensity of the emission light;
wherein the attenuation of the emission light and/or the excitation light by the at least one absorber occurs independently of a quantum yield of the at least one dye.

Furthermore, the present invention relates to a corresponding kit, comprising at least one corresponding dye and at least one corresponding absorber.

Several methods for detecting nucleic acids are known in the prior art. According to these conventional methods, the detection of nucleotides is mostly carried out by dyes. In the following, examples for such conventional methods are mentioned.

For example, intercalating dyes like, for example, Sybr-Green are used in conventional methods, which have a low base fluorescence in case they are not in contact with double-stranded DNA, wherein their fluorescence, however, largely increases in case they are intercalated in double-stranded DNA. A corresponding method, is, for example, disclosed in the document U.S. Pat. No. 5,436,134 A.

Intercalating dyes, like, for example, Sybr-Green, may conventionally be used in a Real-Time PCR or qPCR also for determining the amount of the originally used nucleic acid by determining the point in time or the number of executed cycles at this point in time, wherein the fluorescence, signal of the intercalating dye raises above a specific threshold value. A corresponding method is described in the patent document U.S. Pat. No. 6,569,627 B2. However, corresponding methods often have the disadvantage that the detectable limit or the threshold of detectability, respectively, may be attained only at relatively high concentrations, like, for example, of 10 nM, of the amplificate in typical reaction volumes, whereby the duration of the amplification reaction until the earliest detection point may become very long (for example, if the starting concentration of the template before the amplification reaction is typically in the attomolar range and an amplicon concentration of 10 nM is attained only after many cycles of the amplification reaction).

In other conventional dye-based detection methods for nucleic acids, it is utilized that dyes show a different emission behavior depending on how close they are arranged to another dye or quencher. For example, a quencher may strongly influence the emission behavior of a dye arranged nearby by Förster resonance energy transfer (FRET). On the basis of this principle there are also conventional Real-Time PCR or qPCR methods, like, for example, TaqMan (hydrolysis probes) or hybridizing probes (also called "Light-Cycler-Probes"), which according to the concentration of the amplificate keep (TaqMan) or bring (hybridizing probes) FRET partners in different distances to each other and thus generate differently strong fluorescence signals. Such a method is, for example, described in the patent document U.S. Pat. No. 5,804,375 A.

Other conventional dye-based detection methods for nucleic acids utilize the spatial localization of nucleic acids and render them visible at these locations with dyes, like, for example, in gel electrophoresis or array hybridizing methods.

Furthermore, methods detecting the nucleic acids without using dyes or other markers are known in the prior art. As an example, extinction measurements in the UV range (for example, at a wavelength of 260 nm) allow the determination of the concentration of nucleic acids.

Moreover, further methods using nanoparticles for detecting nucleic acids are known in the prior art. For example, the patent document U.S. Pat. No. 6,812,334 B1 discloses such a method for detecting nucleic acids. According to this method, nanoparticles coupled to oligonucleotides and one or more kind(s) of connection-oligonucleotides are provided. Each connection-oligonucleotide has two sections. The sequence of one section is complementary to the sequence of one of the sections of the nucleic acid and the sequence of the other section is complementary to the sequence of the oligonucleotide on the nanoparticles. The nanoparticle-oligonucleotide-conjugate, the connection-oligonucleotide and the nucleic acid are contacted under hybridization conditions, whereby a measurable change is generated. The above-mentioned patent document further discloses a kit for carrying out said method.

The patent application US 2010/0075335 A1 discloses a colorimetric method for detecting specific nucleic acid sequences, including those of mutations and single nucleotide polymorphisms (SNPs) in nucleotide sequences by aggregation of nanoparticles. In this method identical nanoprobes with oligonucleotides are used, which are directly attached to gold nanoparticles, which are red in solution. The aggregation of these nanoprobes by raising the ionic strength results in a color change from red to blue. The presence of the target DNA to be detected, which has a sequence fully complementary to the sequence of the nanoprobe, prevents said aggregation, whereupon the solution remains red. For example, said method may be used to differentiate between fully complementary sequences and sequences having an SNP. Furthermore, said patent application also discloses a kit for applying said method.

The European patent application EP 1 870 478 A1 discloses a biosensor consisting of metal particles bound to a surface of a support material. A probe molecule, which may in particular be a nucleic acid, which forms a hairpin structure and further has a fluorescent molecule, is attached to said metal particles. Prior to the reaction of the probe molecules with the target molecules the distance between the metal particle and the fluorescent molecule is equal to or less than 5 nm, such that excitation energy is transferred from the fluorescent molecule to the metal particle. Thereby the excited dye may be de-excited without radiating and the fluorescence may be quenched, respectively. The distance between the fluorescent molecule and the metal particle after the reaction and binding, respectively, of the dye with a nucleic acid is typically larger than prior to such reaction and binding, respectively, such that the fluorescent molecule may fluoresce, whereby after that the reaction and the nucleic acid, respectively, may be detected.

Furthermore, the publication R. Gill et al., "*Fast, single-step, and surfactant-free oligonucleotide modification of gold nanoparticles using DNA with a positively charged tail*", Chem. Commun., 2013, 49, 11400-11402 shows how nanoparticles may be functionalized and stabilized with DNA by ZNA. In this context, ZNA means ZIP NUCLEIC ACID, which is distributed by the manufacturer METABION INTERNATIONAL AG, Planegg, Germany and which is described, for example, in document WO 2007 069 092 B1 or WO 2009 083 763 A1.

The thus functionalized nanoparticles may then be specifically connected with other nanoparticles by hybridization and thus generate a measurable optical change. In other words, the use of ZNA according to this conventional method promotes the "adhesion" of the DNA at a nanoparticle. In doing so, the connection of several nanoparticles occurs by a hybridization of DNA, which is coupled to the different nanoparticles. Thus, in this case nucleic acids and nanoparticles are connected by ZNA, i.e. DNA is hybridized to DNA via ZNA.

The methods for detecting a nucleic acid known from the prior art in particular have the disadvantages that the same often have a relatively low sensitivity and that carrying out said methods is often very time consuming, until the presence or absence or the concentration of a specific nucleic acid may be reliably evaluated. Furthermore, conventional methods often require very elaborate detection methods. Furthermore, the manufacturing of the reagents and probes, respectively, used in the prior art is often elaborate and/or their provision is expensive.

Thus, it is the technical problem of the present invention to provide a method and a kit which allow a reliable, sensitive and cost-efficient detection of nucleic acids.

This problem is solved by a method according to the present invention having the steps of claim 1 as well as by a kit having the features of claim 17. Preferred embodiments are subject-matters of the dependent claims.

In a first aspect the invention relates to a method for detecting at least one nucleic acid to be detected in a solution, comprising the steps of:
 providing at least one dye, wherein the solution and/or a reaction vessel, wherein the solution is present, comprises the dye and wherein the at least one dye is adapted to emit emission light due to an optical excitation by excitation light;
 providing at least one absorber in the solution, wherein the absorber is adapted to cause an attenuation of the emission light and/or the excitation light and wherein the attenuation is influenced by a bonding of the at least one absorber to the nucleic acid to be detected; and
 radiating excitation light into the solution and measuring an intensity of the emission light;
wherein the attenuation of the emission light and/or the excitation light by the at least one absorber occurs independently of a quantum yield, in particular independently of a change of a quantum yield, of the at least one dye.

The method according to the present invention provides the advantage that the detection of nucleic acids may be effected particularly efficient. In particular, by a method according to the present invention the time period until a meaningful result is obtained may be significantly reduced.

Furthermore, a method according to the present invention provides the advantage that preferably an implementation in conventional methods for amplifying and replicating, respectively, of nucleic acid can be realized and/or the use of conventional amplification devices and/or conventional detection devices and/or conventional measuring apparatuses is possible and thus optionally no high acquisition costs for suitable devices for carrying out a method according to the present invention are necessary. Furthermore, a method according to the present invention provides the technical advantage that in particular during or within the framework of a detection method in a solution the possibility of a local heating of at least a part of the solution may be combined with a particularly efficient detection method. In this context, local heating refers to the local heating of a solution in close proximity around one or more nanoparticle(s) present in the solution. In particular, a local rise of temperature around the nanoparticle(s) by an optical excitation of the nanoparticle(s) may be generated by said local heating, for example, to specifically cause a reaction by said local heating. This may be used, for example, in the framework of a LASER-PCR, which is described in particular in the document DE 10 2013 215 166 B3.

In one aspect a LASER-PCR may be utilized or used together with or within the framework of the present invention.

Furthermore, the method according to the present invention particularly provides the advantage that at least one dye may be present freely in solution and may have luminescent properties, while it is freely present in solution. In case a dye has luminescent properties, it may in particular be fluorescent and/or phosphorescent and/or be capable to emit light due to other properties.

In particular, according to the present invention it is not necessary for the dye to be connected with the nucleic acid or with the nucleic acid to be detected in order to have luminescent properties and/or to change the luminescent properties. Nevertheless, the change of the measured intensity of the emission light correlates with the presence of the nucleic acid to be detected. In this context, the change of the measured intensity of the emission light is influenced or caused by the binding of the at least one absorber to the nucleic acid to be detected.

Thus, it may be refrained from using intercalating dyes, which often bear a health risk for humans and/or represent an environmental peril.

A further advantage of the present invention is that the luminescence or fluorescence or phosphorescence of the dye is essentially independent from the average spatial distance of the dye to the nucleic acid to be detected and/or the at least one absorber in the solution. In particular, according to the present invention it is not necessary that a dye interacts with a quencher in order to generate a measuring signal for detecting the nucleic acid to be detected. This raises the reliability of the detection of a nucleic acid, since contrary to conventional methods, wherein often quenchers and dyes are used, no maximum distance between a dye and an absorber, in particular not a distance or a spatial distance of merely a few nanometers, has to be provided in order to generate a measuring signal for detecting the nucleic acid to be detected. Furthermore, according to the method according to the present invention no specific spatial geometric arrangement of the dye relative to the absorber is necessary in order to cause an effect on the luminescence of the dye, as it would be case, for example, when using dyes and quenchers.

Preferably, alternatively or additionally to a dye in the solution a dye may be formed in the reaction vessel. In particular, the dye may be formed in a wall and/or in a bottom and/or in a lid of the reaction vessel. In this case, for example, dyes may be incorporated or formed in the reaction vessel and/or a self-luminescence or self-fluorescence or self-phosphorescence or autoluminescence of the material of the reaction vessel may be used. For example, the self-fluorescence may be used, when due to an irradiation with excitation light the reaction vessel has an emission at a longer wavelength as the excitation light. For example, the reaction vessel may at least partly comprise PMMA, which at irradiation with an excitation light at a wavelength of about 400 nm has a fluorescence at a wavelength of 550 nm. For example, the reaction vessel may comprise polypropylene, which, for example, may be optically transparent, in particular for the excitation and/or emission light, or which may be dyed white.

In the framework of the present invention a dye may also be the material of the reaction vessel or comprise the same, which has luminescent, in particular autofluorescent properties.

A further advantage of the method according to the present invention is that the at least one dye does not necessarily have to be functionalized in order to bind to the nucleic acid to be detected and/or to an absorber. In other words, the at least one dye is not necessarily formed as a modification at a DNA probe or at an oligonucleotide. In particular, according to the method according to the present invention the dye does not have to be formed as a DNA probe and/or as a part of a DNA probe. This means that the dye or a nucleic acid attached thereto does not have to hybridize to a single-stranded nucleic acid in order to have or change its luminescent property.

Thus, the method according to the present invention allows to select the dye from a plurality of available dyes, wherein the selection of the dye is not specifically restricted, like, for example, with regard to the requirement that the dye has to be formed intercalating and/or has to interact with a quencher and/or has to be formed as a DNA probe.

A further advantage of the method according to the present invention is that the at least one absorber in the solution may be selected such that the same may cause an attenuation of both the excitation light and the emission light and preferably an attachment of the at least one absorber to the nucleic acid to be detected may cause both a change of the attenuation of the excitation light and a change of the attenuation of the emission light. In this context, the attenuation of the excitation light by the at least one absorber may be caused such that the at least one absorber at least partly absorbs the absorption light and thus less excitation light is available for the optical excitation of the at least one dye, and also such that the absorber may absorb emission light emitted by the dye. Thus, it is particularly advantageous if in case according to a particularly preferred embodiment the at least one absorber is provided such that it may absorb or attenuate both excitation light and emission light. In this context, the attenuation may not only occur by absorption, but also by extinction, i.e. such that also the scattering of excitation light and/or emission light may provide a contribution to the attenuation of the respective light.

In this context, luminescence or fluorescence or phosphorescence means that due to an optical excitation of the dye, in particular by excitation light, at least one photon is absorbed and that, for example, after an at least partial internal relaxation an emission light photon is emitted from the dye.

In case a plurality of dyes is provided, preferably a plurality of identical dyes is provided. Alternatively, such a plurality of dyes may also comprise different dyes. Examples for such dyes are inter alia Cy5, Tamra, Texas Red.

In case a plurality of absorbers is provided, preferably a plurality of identical absorbers is provided. Alternatively, such a plurality of absorbers may also comprise different absorbers.

In this context, the quantum yield is in particular determined by the quotient of the decay rate of the excited state of the dye by spontaneous emission of a photon and the sum of all decay rates of the excited state. In other words, the quantum yield is determined by the decay rate of the spontaneous emission of the excited state of the dye divided by the sum of all decay rates of the excited state of the dye. In other words, the quantum yield is in particular determined by the ratio of the number of emitted emission light photons to the number of absorbed excitation light photons.

In particular, the quantum yield may depend on the lifetime of an excited state of the dye molecule before the same moves on to an energetically lower state, like, for example, the ground state, i.e., it describes how long typically or in the average an excited state of the dye is maintained before the same is de-excited in a radiating recombination process under emission of an emission light photon. The quantum yield may also be determined by the product of the radiating transition rate to the ground state and the lifetime of the excited state.

In particular, the attenuation of the emission light and/or the excitation light by the at least one absorber is in contrast to the use of dyes in combination with quenchers independent from a change of the quantum yield and/or from decay rates of the excited state of the at least one dye. A change of the quantum yield and/or the decay rate of the excited state of the dye or its luminescence, respectively, is not compulsory required for the attenuation of the emission light and/or the excitation light or for the detection of the nucleic acid to be detected according to the present invention. In particular, the attenuation of the excitation light and/or the emission light is achieved by absorption of photons without being necessary for the at least one absorber to interact with the at least one dye at a nanometer scale. For example, it is sufficient for the attenuation of the excitation light and/or the emission light that the at least one absorber is present in the optical path of the excitation light between the light source and the at least one dye or between the emitting dye and the detector, respectively.

Preferably, the quantum yield of the at least one dye or its luminescence, respectively, is essentially independent from the average spatial distance between the at least one dye and the at least one nucleic acid to be detected. This means that in particular for the light emission or the luminescence of the dye no immediate proximity of the dye to the nucleic acid to be detected of, for example, a few Ångstrom or nanometers is necessary, which is in particular in contrast to conventional intercalating dyes and dye-modified DNA probes.

However, other, in particular parasitic, effects may occur, which may have a small influence on the quantum yield without compromising the utilization of the inventive effect. Said effects may, for example, change a non-radiating recombination rate, which will then influence the average lifetime of a non-radiating decay of an excited state of a dye.

Furthermore, the quantum yield may be independent from an average spatial distance between the at least one dye and the at least one absorber, such that, for example, in contrast to a conventional combination of a dye and a quencher the quantum yield is not influenced by a spatial proximity of the dye to an absorber, but the quantum yield of the dye remains independent from the spatial distance to an absorber. Preferably, the quantum yield changes by less than 20% over an average spatial distance of dye and absorber in the range of 10 nm to 1 mm, more preferably of 30 nm to 100 µm, more preferably of 50 nm to 20 µm, in particular of 100 nm to 10 µm. However, also in this case effects, in particular parasitic effects, may occur which may result in a small change of the quantum yield without restricting the use of the effect of the present invention. Furthermore, also non-radiating recombination processes and non-radiating recombination times may have an influence on the quantum yield of the at least one dye, which are then preferably also essentially independent from the average spatial distance of the dye to the nucleic acid to be detected and/or the at least one absorber.

The at least one absorber is preferably formed such that it influences the transmissibility or transmittance or transparency of the solution for the excitation light and/or the emission light, in case the absorber is dissolved in the solution or is present in the solution, respectively. In particular, for this purpose a plurality of absorbers is dispersed essentially homogeneously in the solution and in this way the same determines the macroscopic transmission or transparency or transmissibility at the corresponding absorption wavelength(s) of the absorber. In particular, the absorbers are preferably adapted such that they absorb excitation and/or emission light.

Since no microscopic interaction between dye and absorber is necessary, the excitation light and/or emission light of each dye is attenuated by a plurality of absorbers contained in the surrounding or adjacent solution. According to the present invention, a collective attenuation of the excitation light and/or emission light is effected by the optical density of the solution and not by the (microscopic) interaction of single absorbers with single dyes. Rather, the excitation light and/or emission light of a major part (>50%) of all dyes is respectively attenuated by a plurality of absorbers, preferably at least 5 absorbers, preferably at least 10 absorbers, more preferably at least 100 absorbers and in particular at least 1000 absorbers, respectively. In this case, each absorber typically attenuates the excitation light and/or emission light of a plurality of dyes.

If the at least one absorber binds to the nucleic acid to be detected, this may, for example, result in a change of the macroscopic transmission property of the solution at the excitation light and/or emission light. Thus, in order to detect the nucleic acid to be detected according to the method according to the present invention no microscopic interaction of the dye with the nucleic acid to be detected and/or the at least one absorber is necessary. In particular, the detection of the nucleic acid to be detected does not require an interaction on an Angstrom or nanometer scale of the dye with the at least one absorber and/or the nucleic acid to be detected.

Preferably, the solution wherein the nanoparticles are present has suitable buffer conditions. The buffer conditions may be suitable, if, for example, they allow the process of an amplification reaction for amplifying a nucleic acid.

Preferably, the measurement of the intensity of the emission light is carried out by a measurement of the emission light directly outside of a reaction vessel, wherein the solution is present. Preferably, the excitation light and/or emission light at least partly propagates through the solution before the emission light may be detected or measured, respectively.

The intensity of the emission light may, for example, be measured by a photodetector, like, for example, a photodiode and/or a photomultiplier and/or a spectrometer. Such a photodetector and/or optical elements which may serve to at least partly focus and/or reproduce and/or collimate the emission light exiting the reaction vessel may be arranged, for example, directly adjacent to the reaction vessel. In particular, the distance between the reaction vessel and an optical element and/or a detector, which are used to measure the intensity of the emission light, is only a few millimeters or centimeters, although the distance is not limited thereto.

Particularly preferable it is required for the emission light emitted by the at least one dye to propagate through at least a part of the solution and/or through the reaction vessel or through a wall and/or through the lid and/or through the bottom of the reaction vessel, before the same may be measured or detected directly outside of the reaction vessel. For example, in case the at least one dye is present in the solution in the center of the reaction vessel or in the center of the inner volume of the reaction vessel, wherein the solution is present, in order to be detected or measured by a detector, an emission light emitted at this position at first has to propagate through the solution to a boundary between the solution and the reaction vessel and then through the reaction vessel in order to be then detected or measured by a detector directly outside.

In order to measure the intensity of the emission light, for example, the absolute intensity may be measured by a calibrated detector and/or the intensity of the emission light exiting the reaction vessel compared to a reference value. In this context, the reference value may, for example, be dependent from an intensity of the excitation light which is irradiated into the solution or from a measured value at the beginning of the amplification reaction.

Preferably, the at least one dye is a fluorophore. In particular, the fluorophore comprises a fluorescent dye and/or fluorescent polymer and/or a fluorescent nanoparticle and/or a fluorescent microparticle.

The fluorescent polymer may, for example, comprise a polymer which fluoresces due to an optical excitation, in particular by blue and/or ultraviolet light.

The fluorescent microparticle may comprise or be, for example, a spherule or a pearl or a bead, which is luminescing as such, in particular fluorescing and/or provided with fluorescing substances. For example, such a bead may be a spherule of polystyrene, which is provided with dyes at its surface or wherein dyes are incorporated. For example, dye molecules may be enclosed within such a spherule. In this case it has to be noted that the material of the spherule or of the microparticle should be at least partly transmissible or transparent for the excitation light and the emission light of the dye.

Alternatively or additionally the components of the reaction solution, of the sample or solution to be analyzed and/or of the reaction vessel, which may have a self-fluorescence and/or a self-phosphorescence, may be used as a dye. In particular, it is not necessary for the dyes that the same take part as a reaction partner in a reaction for detecting the nucleic acid to be detected. In particular, it is not necessary that the dye interacts with the nucleic acid or hybridizes therewith.

Alternatively or additionally to fluorescent dyes the dye may comprise a phosphorescent dye molecule and/or a phosphorescent polymer. Alternatively or additionally the dye may comprise fluorescein or consist of fluorescein. The fluorescent nanoparticles may be, for example, semi-conductor nanoparticles and/or semiconductor nanocrystals and/or quantum points or quantum dots and/or metal nanoparticles. Particularly preferable nanoparticles, which are comprised by a dye, consist at least partly, in particular exclusively, of at least one semiconductor material.

Alternatively or additionally the dye may also be a component of the solution, the sample or the reaction vessel having self-fluorescence.

Preferably, a plurality of dyes is provided, which are preferably dispersed essentially homogeneously in the solution.

In particular, preferably a plurality of dye molecules and/or polymers and/or nanoparticles and/or pigments and/or microparticles having fluorescent properties is/are provided in the solution.

The dyes may be added deliberately at least partly into the solution, a sample or the reaction vessel or into parts thereof, without being necessary to be reaction partners of a reaction taking place in the solution or the reaction vessel, like, for example, a PCR reaction, or to interact or hybridize with the nucleic acid. Alternatively or additionally the dyes may already be part of the solution, the sample and/or the reaction vessel or of a part thereof and fulfil a further function besides the fluorescence.

In a preferred embodiment the dye may, for example, be an elongated part connected to the reaction vessel, for example, in the shape of a spike or a sting protruding into the reaction solution and thus may be well surrounded by attenuators. Often the reaction vessel is at least partly fluorescent as such, for example, due to an autofluorescence of the plastic, from which the reaction vessel is at least partly made.

Such an autofluorescence may, for example, in conventional methods, interfere with the actual fluorescence to be detected or the actual desired fluorescence, like, for example, of intercalating dyes or FRET probes, for which reason it is often attempted conventionally to minimize the self-fluorescence or autofluorescence of the reaction vessels R. Also backscattering of excitation light and/or emission light by the reaction vessel R or of parts thereof into the detector may negatively influence the fluorescence actually to be detected in conventional methods. These disadvantages may be avoided particularly efficient by the method according to the present invention in a preferred embodiment, wherein according to a preferred embodiment, both a possible autofluorescence of the reaction vessel and an at least partial scattering or backscattering of excitation light and/or emission light by the reaction vessel may be used directly for the detection without negatively influencing the method.

Preferably, a plurality of absorbers is provided, wherein the plurality of absorbers preferably comprise a particle and/or a nanoparticle, in particular a metallic nanoparticle, and/or a microparticle and/or a pigment and/or a dye molecule.

In this context, nanoparticles are preferably such particles having specific optical properties due to their size. Preferably, said optical properties are mainly provided by the size of the nanoparticles, however, less by their material properties. In this context, the specific optical properties may be, for example, characteristic extinction spectra and/or scattering spectra, which are mainly influenced by the particle size and are not necessarily distinct in the volume material or macroscopic material. Particularly preferable the nanoparticles are such nanoparticles wherein their optical properties are at least partly caused by the plasmonic properties of the nanoparticles. Preferably, the nanoparticles have a diameter of between 2 and 500 nm, more preferably between 3 and 300 nm, more preferably between 5 and 200 nm, still more preferably between 7 and 150 nm, particularly preferable between 10 and 100 nm. The nanoparticles may have a spherical shape, however, their shape is not limited thereto. For example, also other shapes of the nanoparticles are conceivable, like, for example, elongated or rod-like nanoparticles ("nanorods") or also other geometrical shapes.

In a preferred embodiment of the invention at least a part of the nanoparticles comprises at least a metal and/or a semiconductor. In this context, the metal is preferably a noble metal, like, for example, gold, silver, platinum or copper. The semiconductor may, for example, comprise silicon and/or germanium as well as composite semiconductor materials, like, for example, cadmium telluride or lead sulfide. Furthermore, at least a part of the nanoparticles may be composed of different materials. For example, at least a part of the nanoparticles may be formed as a shell-core nanoparticle, wherein, for example, the core comprises a metal and the shell comprises a semiconductor material, or the core comprises a semiconductor material and the shell comprises a metal. In a preferred embodiment all nanoparticles used as an absorber are formed identically and are in particular made from the same material. In a preferred embodiment a nanoparticle may have pores at its surface, which may be occupied by atoms or molecules having a size and charge suitable for the pores, in case, for example, such atoms and/or molecules are present in a solution together with the nanoparticles. In this context, a nanoparticle should also comprise the atoms and/or molecules attached to its surface.

In a particularly preferred embodiment the nanoparticles are suitable to absorb and/or scatter light at specific wavelengths particularly effective due to their specific optical properties. In particular, the nanoparticles absorb or scatter light, the wavelength of which coincides with a plasmon resonance of the nanoparticles, in a particularly effective manner, wherein the wavelength of the plasmon resonance or the excitation energy of the plasmon resonance is mainly determined by the size and/or the shape and/or the material of the nanoparticles. An excitation of the nanoparticles with light, the photon energy of which approximately coincides with the plasmon resonance energy, is suitable in a particularly efficient manner to transmit light energy to the nanoparticles or to have light energy absorbed by the nanoparticles. Nanoparticles comprised by an absorber are particularly preferable at least partly, in particular exclusively, made of at least one metal.

Preferably, at least a part of the plurality of the absorbers is functionalized with at least one functionalizing unit, wherein the functionalizing unit comprises a nucleic acid and is preferably an oligonucleotide, particularly preferable a DNA-oligonucleotide. The oligonucleotide is preferably single-stranded.

In further preferred embodiments different nucleic acids having different nucleotide sequences may respectively be attached to an absorber and/or different nucleic acids having different nucleotide sequences may be attached to different absorbers. In other words, a plurality of absorbers may be present, to which a respective nucleic acid having the same nucleotide sequence is attached, and/or a plurality of absorbers may be present, to which respective nucleic acids having different nucleotide sequences are attached. Furthermore, the absorbers themselves may be different, in particular with respect to their size and/or their shape and/or their material.

In this context, the nucleic acid attached to an absorber of the functionalized nucleic acid, which absorber preferably comprises a nanoparticle, may be attached to the nanoparticle in various manners. In a preferred embodiment the nucleic acid is attached to the nanoparticle by a thiol bond and/or indirectly with a streptavidin-biotin bond and/or with a cationically modified nucleic acid. In this context, further passive nucleotide sequences may be present between an active recognizing sequence of the nucleic acid and the surface of the nanoparticle. Such passive nucleotide sequences may be, for example, spacers and/or non-basic modifications, like, for example, Spacer9, dSpacer, polyethylene glycol and/or similar materials. In particular, passive nucleotide sequences may be formed of the same and/or a similar material, as for example a recognizing sequence or a hybridizing domain of the nucleic acid. For example, such spacers may be formed as DNA-spacers and/or as poly-A-sequence or multi-adenine-sequences. In this context, a Spacer9 is a modification based on a triethylene glycol chain having a length of 9 atoms, as it is well known in the prior art.

In the context of the present invention the terms nucleic acid and oligonucleotide not only comprise deoxyribonucleic acids or DNA-oligonucleotides, but also nucleic acids and oligonucleotides with one or more nucleotide analogs and/or with modifications at their backbone (e.g., methylphosphonate, phosphothioate or peptide nucleic acids (PNAs), in particular at a sugar of the backbone). Furthermore, the same may also contain base analogs, like, for example, 7-deazapurine or universal bases like nitroindole or modified natural bases like N4-ethylcytosine.

In a further embodiment the nucleic acids or oligonucleotides are conjugates or chimeras with non-nucleosidic analogs, like, for example, PNA. The nucleic acids or oligonucleotides may have non-nucleosidic units at one or more position(s), like, for example, spacers, e.g. hexaethylene glycol or $C_n$-spacers, wherein n is preferably a natural number between 3 and 6. In this context, $C_n$-spacers are preferably spacers comprising n carbon atoms. For example, $C_n$-spacers may serve as spacers, in particular between a bonding element, like, for example, a thiol bond, and the nucleic acid as such. For example, $C_n$-spacers may be required for a synthesis of thiol oligomers or may be formed at thiol modifications. In case the nucleic acids or oligonucleotides have modifications, the same are preferably selected such that a hybridization with natural DNA or RNA is also possible with the modification. In further preferred embodiments the nucleic acids and/or the nucleotides may have modifications, which influence the melting behavior, in particular the melting temperature. For example, this may be advantageous in order to differentiate hybrids having different grades of complementarity of their bases (mismatch-discrimination). Further preferred modifications comprise LNA, 8-aza-7-deazapurine, 5-propinyluracil and -cytosin and/or non-basic interruptions or modifications in the nucleic acid or in the oligonucleotide. Further modifications in the sense of the invention are, for example, modifications with biotin, thiol or thiols and fluorescence donor and fluorescence acceptor molecules.

In a particularly preferred embodiment only one or a plurality (of) oligonucleotide(s) is/are bound to the absorber. In case a plurality of oligonucleotides are bound to an absorber, the same may be identical and/or different oligonucleotides. For example, a plurality of different oligonucleotides may be attached to an absorber, respectively. In this context, the oligonucleotides may differ with regard to their length and/or their binding and/or their nucleotide sequence. Preferably, between 1 and 5.000 individual oligonucleotide molecules are bound to an absorber. Particularly preferable, between 2 and 4.000 individual oligonucleotide molecules are bound to an absorber. More preferable, between 10 and 3.000 individual oligonucleotide molecules are bound to an absorber. Still more preferable, between 20 and 2.000 individual oligonucleotide molecules are attached to an absorber. Particularly preferable, between 50 and 1.000 individual oligonucleotide molecules are attached to an absorber.

The larger the number of oligonucleotides attached to an absorber and/or the larger the length or the number of nucleotides per oligonucleotide, which are attached to a nanoparticle, the larger the loading density of the absorber. A larger loading density may cause the advantageous effect that the nanoparticles are more stable in the solution. The absorbers are stable in a solution in particular in case they do not aggregate with each other or clump together and/or precipitate from the solution in particular at room temperature and without external influences. Such an external influence may be, for example, the connection of several absorbers via a nucleic acid. In other words, a large loading density prevents and/or lowers the risk that absorbers aggregate with each other. In a preferred embodiment all stable absorbers present in a solution have at least one molecule attached to their surface. Preferably, the used absorbers have a loading density of between 0.001 and 1, more preferably between 0.001 and 0.5, still more preferably between 0.001 and 0.2, more preferably between 0.001 and 0.1, in particular between 0.01 and 0.1 oligonucleotides per $nm^2$ absorber surface, in particular in case of nanoparticles per $nm^2$ nanoparticle surface.

In this context, an oligonucleotide preferably comprises not more than 1.000 nucleotides, more preferably not more than 500 nucleotides, in particular not more than 200 oligonucleotides, still more preferably not more than 100 nucleotides, still more preferably not more than 80 nucleotides, in particular not more than 50 nucleotides.

Preferably, the at least one functionalizing unit is at least complementary to at least one first sequence section of the nucleic acid to be detected and is adapted to hybridize to a single strand of the nucleic acid to be detected.

In case a first nucleic acid is at least complementary to a second nucleic acid, this means that at least a part of the first nucleic acid is complementary to at least a part of the second nucleic acid. In particular, this means that in case of a complementarity of two nucleic acids their nucleotide sequences are provided such that said nucleic acids may hybridize with each other.

Thus, in case the functionalizing unit is at least partly complementary to the nucleic acid to be detected in the solution, a single strand of the functionalizing unit may hybridize with a single strand of the nucleic acid to be detected in the solution. If the functionalizing unit is hybridized with the nucleic acid to be detected in the solution the nucleic acid to be detected in the solution is connected with or bound to the absorber, to which the functionalizing unit is attached.

If the functionalizing unit is partly complementary to a nucleic acid, this means that at least a part of the functionalizing unit is complementary to at least a part of the nucleic acid. In particular, this means that in case of a complementarity of two nucleic acids their nucleotide sequences are provided such that said nucleic acids may hybridize with each other. Thus, if the functionalizing unit is at least partly complementary to the nucleic acid to be detected in the solution, a single strand of the functionalizing unit, which preferably exclusively comprises single-stranded nucleic acid, may hybridize with a single strand of the nucleic acid to be detected in the solution.

Preferably, each absorber functionalized with at least one functionalizing unit may bind indirectly and/or directly to a further absorber and/or to a reaction vessel by the functionalizing unit via the at least one nucleic acid to be detected.

In a preferred embodiment, the at least one functionalizing unit of a first absorber is at least partly complementary to a first sequence section of a nucleic acid to be detected in the solution and the functionalizing unit of a second absorber is at least partly complementary to a second sequence section of a nucleic acid to be detected in the solution.

For example, the first nucleotide sequence section and the second nucleotide sequence section may be part of the same strand of the nucleic acid to be detected in the solution. If in this case the first and the second functionalizing unit hybridize to the first nucleotide sequence section and the second nucleotide sequence section, respectively, both the first absorber and the second absorber are hybridized or bound to the same strand of the nucleic acid to be detected. In this case, the first and the second absorber are directly bound to each other via the nucleic acid.

In a further preferred embodiment the first nucleotide sequence section is part of the first strand of the nucleic acid to be detected and the second nucleotide sequence section is part of the second strand of the nucleic acid to be detected.

Alternatively or additionally the reaction vessel may have at least one functionalizing unit, which in particular comprises at least one oligonucleotide. In this case, for example, an absorber may be bound directly and/or indirectly to the reaction vessel via its functionalizing unit. Alternatively or additionally an absorber may be bound, via its functionalizing unit, by the nucleic acid to be detected to a functionalizing unit, which is hybridized to the reaction vessel. This may be effected in particular if a first sequence section of the nucleic acid is at least complementary to the functionalizing unit of the at least one absorber and a second sequence section of the nucleic acid is at least complementary to the functionalizing unit of the reaction vessel. For example, the reaction vessel may have one or more functionalizing unit(s) at an inside of the wall and/or at an inside of the bottom and/or lid. In this context, the inside should be the side which is in contact with the solution, provided that the solution is present in the reaction vessel. For example, absorbers may be immobilized or attached at the reaction vessel.

Preferably, a binding of at least two of the plurality of absorbers together causes a sedimentation of the respective bound absorbers and/or a change of an absorption efficiency of the bound absorbers for the excitation light and/or the emission light and/or a binding of an absorber of the plurality of absorbers with the reaction vessel causes an immobilization of the respective absorber.

In this context, immobilization means that the immobilized absorber is restricted with regard to its mobility in view of the object at which it is immobilized, like, for example, at the reaction vessel. For example, an immobilized absorber may have a mobility in at least one spatial direction of merely less than 10 µm, preferably less than 1 µm, particularly preferable less than 0.1 µm. Particularly preferable the mobility of the absorber is restricted in two spatial directions, in particular in all three spatial directions.

In this context, sedimentation means that the respective bound absorbers precipitate from the solution. For example, this may result in that the sedimenting or precipitating absorbers collect as solid particles at a specific location in the solution. For example, the same may collect at the bottom of the reaction vessel due to gravity. For example, the sedimentation may be caused by a reduction of the average distance of respective bound absorbers or by the average distance of respective bound absorbers becoming so small in a manner that the same clump together and thus precipitate from the solution. This may, for example, change a macroscopic property of the solution, like, for example, its transmissibility for the excitation light and/or the emission light. The transmissibility of the solution may change in particular because a smaller number of absorbers are homogeneously dispersed in the solution or because of a lower concentration or density of absorbers is present in at least a partial volume of the solution. Those parts of the solution, which then locally have a lower concentration of absorbers, may have, for example, a larger transmissibility or transparency of excitation light and/or emission light.

Furthermore, the binding of at least two of the plurality of absorbers to each other may cause a change of the absorption efficiency for excitation light and/or emission light of the respective bound absorbers. For example, this may be caused by a reduction and/or shift of the absorption due to plasmon resonance due to a reduced or small distance between the bound absorbers, typically in the range of 1 nm to 100 nm, because of a plasmon interaction between the bound absorbers. For example, a red shift of at least a part of the absorption spectrum of the absorber may occur, whereby the absorption efficiency of the respective absorbers for the excitation light and/or the emission light is reduced.

Similar to the sedimentation of respective bound absorbers also a sedimentation of absorbers at the reaction vessel may influence the homogeneity of the dispersion of absorbers in at least a part of the solution. If, for example, a part of the absorbers is sedimented at the reaction vessel or at the boundary between the solution and the reaction vessel, the local density or concentration of the absorber in other parts of the solution may be lowered and thus the transmissibility of the solution for the excitation light and/or the emission light may be reduced in these parts of the solution.

In the framework of the invention, these effects may be used separately and/or also combinations thereof may be used. In particular, it may be sufficient to utilize one or more of the indicated effects.

Preferably, the sedimentation of the respective absorber and/or the change of the absorption efficiency of the connected absorbers and/or the immobilization of the respective absorber at least partly in the solution causes a change of the attenuation of the excitation light and/or the emission light.

Preferably, the at least one dye is formed as fluorescent microparticle, which is functionalized with at least two oligonucleotides, which are at least partly complementary to at least a second sequence section of the nucleic acid to be detected, wherein the second sequence section overlaps at least not completely with the first sequence section.

In this manner, at least one absorber, respectively, may be bound to each of the at least two oligonucleotides, which are functionalized to the fluorescent microparticle, in particular via the nucleic acid to be detected. In this context, the nucleic acid to be detected may act as connection nucleic acid.

Preferably, the fluorescent microparticle comprises at least ten oligonucleotides, more preferably at least 100 oligonucleotides, still more preferably at least 500 oligonucleotides, in particular at least 1000 oligonucleotides.

If at least one absorber connects to at least a part of the oligonucleotide or the functionalizing units, which are functionalized to the fluorescent microparticle, for example, the fluorescent microparticle may be at least partly shielded from the excitation light. In this manner, a smaller number of optical excitations in the shielded fluorescent microparticle results. Due to this reduced number of optical excitations also the emission of emission light by the fluorescent microparticle decreases. Furthermore, the emission light nevertheless emitted from the fluorescent microparticle may preferably be also at least partly absorbed by the absorber bound with the fluorescent microparticle.

Thus, in case a nucleic acid to be detected is present in the solution, this may result in a significant reduction of the emission of emission light by the dyes formed as fluorescent microparticles. According to a particularly preferred embodiment, this occurs in a particularly efficient manner on the one hand by a particularly efficient shielding of the respective dye from the excitation light and on the other hand since the emission of emission light by the respective dye, which occurs anyhow, is in addition at least partly absorbed by the absorbers bound thereto according to a particularly preferred embodiment.

By the fact that the first sequence section and the second sequence section at least do not fully overlap, it may be secured that both an absorber and the oligonucleotide of the fluorescent microparticle may attach or hybridize to the nucleic acid to be detected, without essentially interfering with each other.

Preferably, the optical excitation of the dye and/or the emission of emission light by the dye is attenuated, if at least two absorbers, which are respectively functionalized with at least one functionalizing unit, are bound to the dye or to the fluorescent microparticle and are preferably immobilized at the dye or at the fluorescent microparticle.

Particularly preferable the at least two absorbers are bound to the dye or to the fluorescent microparticle via the nucleic acid to be detected.

According to a preferred embodiment the method is used for detecting the nucleic acid to be detected in the solution, wherein the method preferably comprises a replication of the nucleic acid to be detected.

Preferably, the detection of the nucleic acid to be detected is carried out during and/or after an amplification or replication of the nucleic acid to be detected in the solution, wherein the amplification or replication is preferably carried out by a PCR.

In particular, the detection of a nucleic acid to be detected in the solution may be effected such that not or not only the original nucleic acid or the nucleic acid present at the beginning as such is detected, but alternatively or additionally the amplificates or duplicates of the original nucleic acid generated in a replication reaction or amplification reaction. This may, for example, allow that a nucleic acid may be detected in the solution having an initial concentration too low to be able to elicit a measurable effect or a measureable change of the intensity of the emission light without prior replication. In particular, an amplification reaction may be advantageous in case the change of the intensity of the emission light generated by the originally present nucleic acid to be detected is not sufficient in order to reliably detect or measure said change compared to a solution without nucleic acid to be detected.

According to a preferred embodiment a PCR may have several cycles, wherein a cycle preferably includes the steps of denaturing, annealing and elongation. Preferably, the cycle or the steps comprised by the cycle is/are passed through several times during a PCR.

In particular, the denaturing during a PCR may be effected by a global and/or local heating of the solution. In this context, a global heating of the solution means that essentially the whole solution is homogeneously heated, whereas by a local heating merely one or more partial volume(s), for example, around nanoparticles, is/are heated by an optical excitation of the respective nanoparticles. For example, by global heating the solution may be heated to a temperature below the denaturing temperature or held at such temperature by global heating. Furthermore, starting from that the temperature in partial volumes of the solution may be raised to the denaturing temperature or a higher temperature by local heating. A corresponding local heating is described, for example, in the document DE 10 2013 215 166 B3.

A global heating of the solution may be effected, for example, by a heating of the whole solution or at least a part of the reaction vessel, in which the solution is present.

The method according to the present invention may, for example, either be used as an endpoint detection after the end of the amplification method or as a real-time method during the amplification reaction, which then preferably allows a quantification of the originally present nucleic acid concentration in the sample.

Preferably, during a real-time PCR not more than 200 cycles, more preferably not more than 150 cycles, still more preferably not more than 100 cycles, more preferably not more than 60 cycles, still more preferably not more than 40 cycles, particularly preferable not more than 30 cycles, most preferably not more than 25 cycles are passed through.

In this context, the amplification or replication or PCR may be preferably effected in the same solution, wherein the at least one dye and the at least one absorber are present. According to a particularly preferred embodiment the method according to the present invention for detecting at least one nucleic acid to be detected in the solution may also be carried out in instruments or apparatuses conventionally used for carrying out a PCR. In particular, the method according to the present invention for detecting at least one nucleic acid to be detected may be carried out in the framework of a real-time PCR preferably in a LIGHTCYCLER apparatus (of the manufacturer ROCHE DIAGNOSTICS).

In a preferred embodiment, in particular within the framework of a LASER-PCR, by an excitation of at least a part of the absorbers, which according to this embodiment are at least partly formed as a nanoparticle, a surrounding of the excited nanoparticle is locally heated. In this context, nanoparticles, which have to be excited for locally heating the solution do not necessarily have to be the same or identical particles as the nanoparticles used for the attenuation of the exciting light and/or the emission light. For example, the nanoparticles may differ with regard to the oligonucleotides or functionalizing units bound thereto and/or the materials and/or the shape and/or the size.

Preferably, the excitation of a nanoparticle occurs by an optical excitation. The optical excitation of a nanoparticle may occur, for example, by the absorption of photons by the nanoparticle. The absorption of a photon by a nanoparticle is specifically efficient if the photon energy approximately corresponds to the excitation energy of a plasmon in the nanoparticle or the plasmon resonance of the nanoparticle. In particular, the photon energy essentially corresponds to the plasmon excitation energy if at least a partial overlap is present between the plasmon absorption band and the wavelength spectrum of the photon or the incident light. The larger the spectral overlap of the incident light with the plasmon absorption spectrum, typically the larger the absorption cross section of the optical excitation of the nanoparticles by the incident light.

In case heat is transferred to the surrounding of the nanoparticle by excitation of a nanoparticle, this means that energy is transferred to the nanoparticle and the nanoparticle heats its surrounding by an energy transfer. By the excitation of the nanoparticle preferably the immediate surrounding of the nanoparticle is heated more strongly than the farther surrounding of the nanoparticle. Typically, the nanoparticle is initially heated by excitation, in particular by optical excitation, and then transfers the heat to its surrounding, in which the temperature is at least 5° C. higher than before the excitation. Preferably, the surrounding of the nanoparticle is a spherical volume having approximately one hundred times (100-times) the diameter of the nanoparticle, which is located in the center or center point of this volume. Particularly preferable, the volume has about ten times the diameter, more preferably about four times the diameter, in particular less than twice the diameter of the nanoparticle.

Preferably, by the excitation of a plurality of nanoparticles the surrounding of the plurality of nanoparticles is locally heated. Particularly fast temperature changes are possible in particular in case the heated volume represents only a small fraction of the total volume of the solution, wherein the nanoparticles are present. On the one hand, in this case a high temperature difference may be generated already with a small energy introduction by the radiation or by the light. On the other hand, a very fast cooling of the heated volume is possible if a sufficiently large cold temperature reservoir is present in the irradiated volume or around the irradiated volume, in order to cool the nanoparticles and their surrounding again after the irradiation. This may be effected, for example, in that the nanoparticles are irradiated sufficiently strong (in order to achieve the desired increase in temperature) and sufficiently short (such that the heat remains localized). In an advantageous manner it is possible to subject the polymerases, which may also be present in the solution, to a smaller heat or heat dose or heat introduction by a local heating, such that also PCR methods having a cycle number of more than 80 may be realized.

For example, such an optical excitation of the nanoparticles may be effected by laser radiation, wherein the photon energy preferably essentially corresponds to the excitation energy of a plasmon resonance of the at least one part of the nanoparticles. Preferably, the excitation is effected by absorption of light or laser radiation by at least a part of the nanoparticles. A local heating is present in particular if the duration of the optical excitation in the respective irradiated volume (e.g., in the laser focus) t is selected to be shorter or equal to a critical excitation duration t1. In this context, t1 is determined by a time the heat needs to diffuse from one nanoparticle to the next nanoparticle at an average nanoparticle distance, multiplied by a scaling factor s1. In case of an average nanoparticle distance |x| and a temperature conductivity D of the medium between the nanoparticles, the critical excitation duration t1 is given by $t1=(s1 \cdot |x|)^2/D$, wherein the temperature conductivity D typically has a value of $D=10^{-7}$ m$^2$/s in an aqueous solution. In this context, the scaling factor s1 is preferably s1=100, particularly preferable s1=10, particularly preferable s1=1 and more preferable s1=0.1. For the definition of the local heating the average nanoparticle distance in meters is $|x|=(C_{NP} \cdot 1000 \cdot NA)^{-1/3}$, wherein $C_{NP}$ is the molar concentration of the nanoparticles and NA represents the Avogadro constant.

Preferably, the detection of the nucleic acid to be detected is carried out in the framework of a real-time PCR.

In particular, the occurrence of a measureable change of the intensity of the emission light in a real-time PCR may be used to determine the initial concentration of the nucleic acid to be detected from the consecutive number of the cycle, wherein said measurable change of the physical property of the solution occurs.

In contrast to conventional real-time PCR methods the method according to the present invention may result in an earlier detectability, i.e. a lower number of cycles, of the optionally amplified nucleic acid to be detected and/or to a more significant, in particular steeper, raise of the signal. This may, for example, allow a faster, improved and/or more reliable detection of the nucleic acid. A further advantage of the method according to the present invention may be that polymerase concentrations which preferably correspond to not more than 20%, particularly preferable not more than 5% of the amount or concentration of polymerases typically recommended by the manufacturer of the polymerase, may be sufficient.

In a further preferred embodiment, the intensity of the emission light is measured at different temperatures of the solution.

For example, measuring the intensity of the emission light at different temperatures may serve to determine the complementarity of two nucleic acids present in the solution. The larger the complementarity of two nucleic acids present in the solution, typically the higher their melting temperature, in case the same are hybridized to a double strand. In this manner, for example, it may be determined at which temperature the melting point of two complementary or at least partly complementary nucleic acids is in the solution and/or at which temperature the melting point is exceeded, by selective, successive risings of the temperature. Furthermore, measuring the physical property of the solution at different temperatures may serve, for example, for at least partly determining a sequence composition and/or length of two nucleic acids present in the solution. For DNA it has to be typically assumed that the larger the length and the GC content, i.e. the ratio of guanine-cytosin base pairs, of two nucleic acids present in the solution, typically the higher their melting temperature if they are hybridized to a double strand. Preferably, the melting curve when applying according to the present invention the method according to the present invention is sharper or more clearly visible or has less noise than a melting curve recorded with a conventional method. In other words, according to a preferred embodiment, with the method according to the present invention the full width at half maximum of the first derivative of the melting curve is preferably lower. Preferably, the full width at half maximum of the first derivative of the melting curve is less than 7° C., more preferably less than 5° C., still more preferably less than 3° C. and in particular less than 2° C. A steep melting curve or in other words a small full width at half maximum of the first derivative of the melting curve may be advantageous in order to be able to better differentiate between melting points or melting temperatures of different nucleic acids, in case the same lie closely together or in case the melting points or melting temperatures are not much different.

Preferably, at least a part of the plurality of absorbers is respectively functionalized with at least one functionalizing unit, wherein the functionalizing unit is an oligonucleotide and the oligonucleotide at least partly serves as a primer, like, for example, as forward primer or as reverse primer.

For example, the oligonucleotide or the functionalizing unit bound to the absorber may be a forward primer or a reverse primer for a first strand of the nucleic acid to be detected. Furthermore, an oligonucleotide bound to the dye or the functionalizing unit attached thereto may be a forward primer or a reverse primer for a second strand of the nucleic acid to be detected.

According to this preferred embodiment, preferably the oligonucleotide bound to the absorber is elongated during an amplification process during an amplification reaction. The correspondingly generated amplificates may then preferably hybridize with each other, wherein preferably the hybridization of an elongated oligonucleotide bound to an absorber with an elongated nucleic acid of a different absorber may occur.

During an annealing process of a PCR the primers may hybridize with the first strand and/or the second strand of the nucleic acid to be detected. In this case, the oligonucleotide bound to the absorber may comprise further parts or blocks or sections, which do not essentially contribute to the function as a primer. For example, the same may be one or more section(s) of the oligonucleotide, by which the oligonucleotide is bound to the absorber. Furthermore, the oligonucleotide may have one or more spacer(s), which do not essentially contribute to the functionality as a primer.

In a preferred embodiment, at least a part of the at least one oligonucleotide or the functionalizing unit has one or more terminal modifications at the 3' end, like, for example, dideoxycytidin (ddC) or phosphate or biotin. These modifications may prevent the 3' extension of the at least one part of the at least one oligonucleotide by the polymerase, such that the at least one part of the at least one oligonucleotide cannot serve as a primer. This may be advantageous in order to influence and/or disturb the amplification process as little as possible by the presence of the oligonucleotide and/or to use the oligonucleotide as hybridizing probe or DNA probe.

In this context, a hybridizing probe or DNA probe designates in particular a nucleic acid and/or a part of a nucleic acid and/or a nucleotide sequence section of a nucleic acid, wherein by the hybridization of which with at least a part of the nucleic acid to be detected the presence of the respective nucleic acid to be detected may be checked or detected, wherein the hybridizing probe may preferably hybridize, but is not elongated.

According to a particularly preferred embodiment, a nucleic acid to be detected in the solution may serve as a target, for example, in order to elongate the primer(s) in the course of an amplification reaction, i.e. to elongate the nucleic acid connected with an absorber. Furthermore, the solution may contain a further nucleic acid, which also serves as a primer, like, for example, as a reverse primer, and which is also elongated during the amplification reaction. According to this preferred embodiment the absorbers connected with the nucleic acid and/or further absorbers may also serve as hybridization probes. In this context, a hybridization probe in particular designates a nucleic acid and/or a part of a nucleic acid and/or a nucleotide sequence section of a nucleic acid, wherein by hybridization thereof with at least a part of the nucleic acid to be detected the presence of the respective nucleic acid to be detected may be checked or detected, wherein the hybridization probe may preferably hybridize, but is not elongated.

Preferably, according to this preferred embodiment, the amplification reaction alone, for example, in the absence of a hybridization probe and/or in the absence of a nucleic acid to be detected, does not result in a sufficient measurable change of the intensity of the emission light of the solution. If, for example, the corresponding complementary counterpart to the absorber-bound nucleic acid or to the hybridization probe was generated during the amplification reaction in the elongated part at a different absorber, for example, the absorber-bound hybridization probe may hybridize with the other absorber at the part at the forward primer elongated during the amplification reaction and result in a compound of the absorber-bound hybridization probe having the forward primer with the further absorber.

Preferably, a measurable change of the intensity of the emission light occurs starting from a sufficient amount of amplicon or elongated nucleic acid with absorber.

For example, this method may be either used as an endpoint detection after the end of the amplification method or as a real-time method during the amplification reaction, which then preferably allows a quantification of the originally present nucleic acid concentration in the sample. In this context, it may optionally be preferable to select the amount of the reverse primer to be lower than the amount of forward primer with absorber. This may, for example, be advantageous in order to generate an excess of the nucleic acid strand during the amplification reaction, which is generated by elongation of the forward primer (single-stranded part of the amplicon), to which the absorber-bound hybridization probe may hybridize, without resulting, for example, in a competition with the counter-strand (single-stranded part of the amplicon generated by elongation of the reverse primer).

Preferably, the recognition sequence or hybridization probe sequence and the primer sequences or nucleotide sequences, which serve as primers, do not overlap. Preferably, no contiguous subsection of the recognition sequence or hybridization probe sequence of more than 7 nucleotide bases, more preferably of more than 5 nucleotide bases, more preferably of more than 3 and in particular of more than 2 nucleotide bases is complementary to or identical with the primer sequences or the nucleotide sequences serving as a primer. Preferably, the nucleotide sequence of the hybridization probe, i.e. the hybridization probe sequence, ist modified at least at the 3' end (e.g., by biotin, phosphate, ddC or other modifications, which prevent an elongation by the polymerase) or carries a dangling 3' end, which is non-complementary to the target sequence with at least one base. Thus, it may be prevented, for example, that the hybridization probe sequence is involved in the exponential amplification, comparable, for example, with a TaqMan probe.

This preferred embodiment may, for example, have the advantage that the forming of primer dimers may be reduced and/or prevented. In particular, it may be prevented or at least partly avoided that the forming of primer dimers results in a connection of at least two absorbers. This may contribute to the formation of a signal by mistake in an advantageous manner, although no nucleic acid to be detected is present in the solution. In particular, this may contribute to avoiding a signal emerging by mistake in that the hybridizing probe, i.e. the nucleic acid, which is at least partly complementary to the nucleic acid to be detected or at least partly identical with the nucleic acid to be detected, i.e. the nucleic acid bound to an absorber according to this preferred embodiment, is not substantially amplified.

In a further aspect the invention relates to a kit for detecting at least one nucleic acid to be detected in a solution, comprising:
  at least one dye for introducing into the solution, wherein the at least one dye is adapted to emit emission light due to an optical excitation by excitation light; and
  at least one absorber for introducing into the solution, wherein the absorber is adapted to effect an attenuation of the emission light and/or the excitation light, and wherein the attenuation is influenced by the bonding of the at least one absorber to the nucleic acid to be detected;
wherein the attenuation of the emission light and/or the excitation light occurs independently of the quantum yield of the at least one dye.

Preferably, the kit comprises a dye and an absorber as defined before for the method according to the present invention, in particular according to one of the above-described preferred embodiments.

The absorber on the one hand and the dye on the other hand may be present separately in the kit or be separately packaged. In a preferred embodiment, the absorber is present in a first solution and the dye is present in a second solution different from the first solution. For example, the first and the second solution are mixed by the user only in case a method according to the present invention should be carried out. Alternatively, the absorber and the dye may be present together also in one single solution.

The invention relates to the qualitative and/or quantitative detection of nucleic acids having an at least partly known nucleotide sequence. Furthermore, the invention relates to the detection or determination of a deviation of a nucleotide sequence of a nucleic acid from a predetermined nucleotide sequence.

In particular, in one aspect the invention relates to the detection of the presence and/or the concentration of nucleic acids, like, for example, deoxyribonucleic acids (DNA) or ribonucleic acids (RNA). The detection may then provide information, for example, whether a germ was present in a sample to be tested and/or whether a human or animal/organism has a specific genetic predisposition or not. In such a nucleic acid detection the nucleic acid sequence to be detected is fully or at least partly known previously. Alternatively, for example, an objective may be merely the detection of the presence of a nucleic acid sequence to be detected in a sample and/or the determination of optional variations or deviations of the sequence from a predetermined sequence.

Furthermore, in the framework of the invention a detection of a nucleic acid may be carried out directly, i.e. in case the amount of the nucleic acid to be detected is sufficient, for example, without a previous e.g. enzymatic replication, like, for example, a polymerase chain reaction (PCR) and/or an isothermal amplification and/or a previous transcription like, for example, a reverse transcription (RT).

Furthermore, the invention may also relate to an indirect detection of the nucleic acids, i.e., for example, a detection after and/or during an enzymatic replication reaction such as PCR and/or an isothermal amplification. This may be desirable in case the nucleic acid to be detected is present, for example, merely in small amounts in a sample to be tested and thus has to be replicated at first, in order to be then present for a detection reaction in a sufficient amount. In this case, it may be e.g. advantageous if the reaction to be detected occurs only starting from a certain minimum amount of a nucleic acid to be detected or replicated and/or provides a detectable signal and thus the point in time of the occurrence of the detection reaction or the first signal detection during a replication reaction may be used as a measure for the amount of the originally present nucleic acid (for example, real-time PCR or qPCR). An indirect detection of nucleic acids may also mean that before the actual detection a further step, like, for example, a previous RT is carried out, i.e. a transcription of RNA into DNA.

In the following, single preferred embodiments for solving the underlying technical problem are described in an exemplary manner referring to the Figures. In this context, the described embodiments partly have features that are not compulsory necessary to carry out the claimed subject-matter or the claimed method, however, which provide desired properties in specific application cases. For example, also embodiments which do not include all features of the embodiments described in the following should be regarded to be covered by the described technical teaching. Furthermore, in order to avoid unnecessary repetitions, specific features are mentioned only in reference to single embodiments described in the following. It should be noted that the embodiments should not only be regarded as such, but also in a synopsis. According to this synopsis the skilled person will recognize that single embodiments may be modified also by introducing one or more features of other embodiments. It should be noted that a systematic combination of the single embodiments with single or several features described with regard to other embodiments, may be desirable and reasonable and thus should be considered and also regarded as being covered by the description.

BRIEF DESCRIPTION OF DRAWINGS

There are showing:
FIGS. 3A, 3B, 3C, 3D and 3E: show a graphic representation of extinction spectra of absorbers when carrying out a method according to a preferred embodiment;
FIGS. 4A, 4B-1, 4B-2, 4C-1, and 4C-2: show schematic representations of the mode of operation of preferred embodiments of the method according to the present invention.

FIG. 1A shows a schematic representation of an absorber 1 comprising a nanoparticle 2 in a method according to the present invention according to a preferred embodiment. According to a preferred embodiment, a plurality of oligonucleotides 4, which serve as functionalization unit, is functionalized to the nanoparticle 2.

According to the preferred embodiment, the functionalization units 4 are formed as an oligonucleotide 4. In this context, all oligonucleotides 4 functionalized to the nanoparticle 2 may have the same nucleotide sequence or different nucleotide sequences. The oligonucleotides 4 may be the same or different and bound to the nanoparticle 2 in the same or different orientation. FIG. 1A shows the nanoparticle 2 merely in a two-dimensional projection or in a two-dimensional cross-section. The oligonucleotides 4 are preferably dispersed over the whole surface of the three-dimensional, preferably spherical, nanoparticle 2. Most preferably, the nucleic acids 4 attached to the nanoparticle 2 are single-stranded oligonucleotides 4 or single-stranded nucleic acids and selected such that the same do not hybridize with other nucleic acids 4 bound to the nanoparticle(s) 2. Particularly preferable all nucleic acids 4 bound to the nanoparticles 2 are the same nucleic acids 4.

The change of the attenuator properties in the presence of or starting from a specific concentration of the nucleic acid to be detected may be generated, for example, such that at least two attenuators change their distance between each other by the nucleic acid to be detected and as a consequence their absorption or scattering properties change. The attenuator properties may, for example, change, while the attenuators stay homogeneously (or relatively homogeneous in contrast to a sedimentation or immobilization) dispersed in the reaction solution. For example, the attenuators may be at least partly gold nanoparticles, which are connected by the nucleic acid to be detected, such that the plasmon resonances are spectrally shifted by a coupling of plasmons of or in or on two nanoparticles. This may cause, for example, a changed attenuation of the excitation light and/or the emission light. Nanoparticles may, for example, be provided with oligonucleotides, which by hybridizing with the nucleic acid to be detected and/or with other oligonucleotides, which are also attached on nanoparticles, result in a connection of nanoparticles or in a prevention of the connection of nanoparticles.

Alternatively or in addition at least two attenuators may be sedimented by the nucleic acid to be detected. This may cause a changed attenuation of the excitation light and/or the emission light, since the attenuators then, for example, are not necessarily homogeneously dispersed in the reaction solution anymore. For example, nanoparticles may be connected with each other by the nucleic acid to be detected and thus a sedimentation thereof may be caused.

Figure 1A:
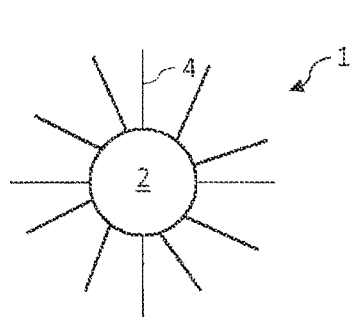
FIGS. 1A, 1B-1, 1B-2, 1C, and 1D show schematic representations of preferred embodiments of absorbers as well as preferred embodiments of the method according to the present invention.
Figures 1, 1B:
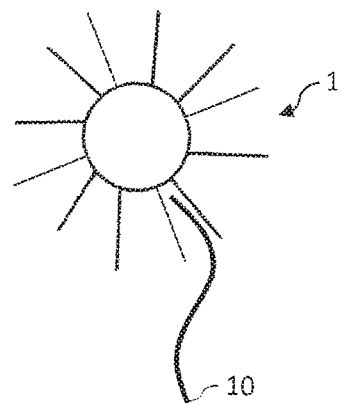

As shown in FIG. 1B1, in particular according to a first preferred embodiment at least two different kinds of absorbers 1 may be used, which, for example, each comprise a nanoparticle 2, which differ at least in the nucleotide sequences of their functionalization units 4. For example, a first kind of the absorbers 1 may be formed such that the functionalization unit 4 of this first kind of absorbers 1 is at least partly complementary to a first sequence section of a single-stranded nucleic acid to be detected 10 and may hybridize with the first sequence section of the nucleic acid to be detected 10. Furthermore, a second kind of the absorbers 1 may be formed such that the functionalization unit 4 of this second kind of absorbers 1 is at least partly complementary to a second sequence section of a single-stranded nucleic acid to be detected 10 and may hybridize with the first sequence section of the nucleic acid to be detected 10. In this manner, for example, an absorber 1 of the first kind and an absorber 1 of the second kind may be connected or bound via the nucleic acid 10, if these absorbers hybridize with the nucleic acid 10. This may, for example, result in that the distance of the surfaces of the nanoparticles 2 of the connected absorbers 1 becomes so small, for example, smaller than 30 nm, such that a red shift of the extinction spectrum of the connected nanoparticles occurs at least partly. In this context, the distance of the surfaces of the nanoparticles should be the shortest distance of the surfaces of the nanoparticles, i.e., the distance of the points of the two surfaces of the two nanoparticles closest to each other. Alternatively or additionally an aggregation or sedimentation or precipitation of the nanoparticles 2 or the absorbers 1 from the solution may occur at least partly due to the connection of the absorber 1 or the nanoparticle 2 by the nucleic acid 10.

Alternatively or additionally the connection of absorbers 1 with a nucleic acid to be detected 10 may also result in an aggregation of absorbers 1, although the absorbers 1 are not immediately connected via the nucleic acid. For example, by a connection of absorbers with at least one nucleic acid, respectively, a change of the stabilization of the absorbers in solution may result, such that the same, if they are connected with the nucleic acid, preferably aggregate with other absorbers and/or precipitate from the solution. This is shown schematically in FIG. 1B-2. In particular, by the connection of absorbers 1 with at least one nucleic acid to be detected 10, respectively, an electrostatic interaction between absorbers may change, which allows an aggregation and/or a precipitation and/or a sedimentation of the absorbers 1.

This may, for example, be additionally promoted and/or influenced by a cationically modified nucleic acid in the solution. For example, a cationically modified nucleic acid may be connected with an absorber 1 via a nucleic acid to be detected and influence its electrostatic charge.

In this context, the cationically modified nucleic acid is preferably a nucleic acid including a cationic block or a cationic section. It may be, for example, a nucleic acid having a cationic extension at least at one end thereof. The cationic extension preferably has an average charge density, which is less anionic as the average charge density of a nucleic acid, in particular in case both the nucleic acid and the cationic extension are present in an environment typical for the nucleic acid. In other words, the cationic extension is electrically charged preferably more positive than a nucleic acid. The nucleic acid having a cationic modification or the cationically modified nucleic acid further comprises preferably a section or a hybridization region, which mainly comprises a nucleic acid and a cationic extension conjugated thereto.

In a preferred embodiment the cationic extension of the cationically modified nucleic acid comprises cationic spermines. In this case, the cationic extension comprises between 1 and 20 spermines, preferably between 2 and 15 spermines, particularly preferable between 2 and 10 spermines, in particular between 2 and 5 spermines. The average electrical charge density of a cationically modified nucleic acid is less anionic than the average electrical charge density of a non-cationically modified nucleic acid. In this manner, for example, the electrostatic repulsion between a cationically modified nucleic acid and a non-cationically modified nucleic acid is smaller than the electrostatic repulsion between two non-cationically modified nucleic acids. Particularly preferable, a cationically modified nucleic acid and a non-cationically modified nucleic acid attract each other electrostatically.

For example, a cationically modified nucleic acid comprises a nucleic acid of the type of a ZIP NUCLEIC ACID (ZNA) of the manufacturer METABION (METABION INTERNATIONAL AG, Planegg, Germany), which is described, for example, in document WO 2007 069 092 B1 or WO 2009 083 763 A1. Alternatively or additionally, a cationically modified nucleic acid may comprise at least a cationically charged dye and/or other cationic units. Adding at least one cationic unit to a nucleic acid is preferably effected at the 5' terminus and/or at the 3 terminus of the nucleic acid.

Figure 1C:
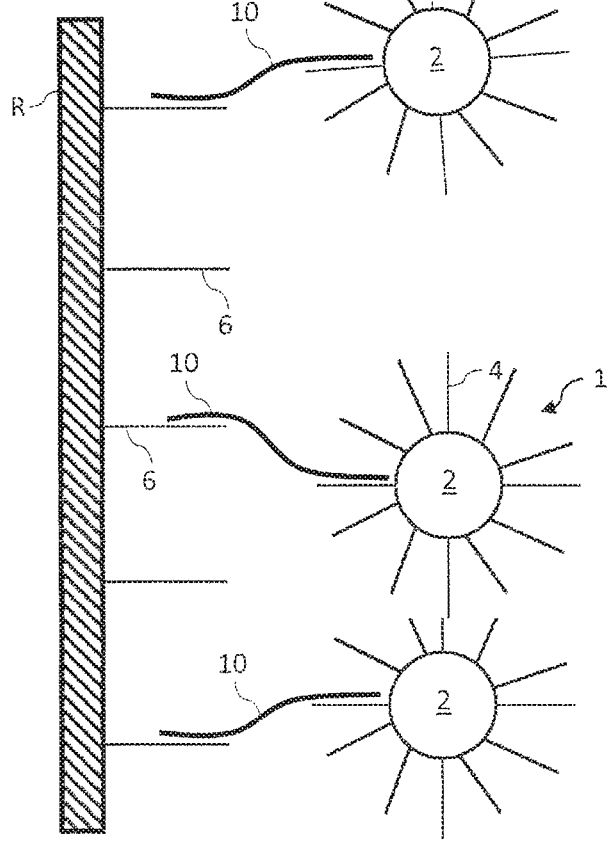

According to a second preferred embodiment, which is schematically shown in FIG. 1C, the reaction vessel R may have at least one functionalizing unit 6. In FIG. 1C only a part of a wall, like, for example, a sidewall, of the reaction vessel R is shown, which has a plurality of functionalizing units 6. According to this preferred embodiment, the reaction vessel R may serve as immobilizing unit. The functionalizing units of the reaction vessel R serving as immobilizing unit are bound at least partly at a part of the reaction vessel R or at its wall, which is in contact with at least a part of the solution, wherein the dyes 8 and the absorber 1 are present.

As a consequence, alternatively or additionally to a connection of at least two attenuators 1 with each other as a consequence of the presence of the nucleic acid to be detected, also an immobilization of at least two attenuators at a specific location in the reaction solution and/or the reaction vessel, in particular via a nucleic acid to be detected 10, may occur. For example, absorbers 1 (which were e.g. homogenously dispersed in the reaction solution before or without nucleic acid to be detected) may be specifically bound to the sidewalls of the reaction vessel by the nucleic acid to be detected 10, where they remain against the effect of gravity. In case of an irradiation of excitation light and/or the measurement of emission light is effected from above and/or below, less or no attenuators influence the excitation light and/or the emission light of the dyes, which are further distant from the wall of the reaction vessel than the immobilized absorber 1, in contrast to absorbers homogeneously dispersed in the solution.

The immobilization may, for example, be effected in that the absorbers are provided with at least one oligonucleotide 4a having the sequence A, which is at least partly complementary to a first subsection of the nucleotide sequence of the nucleic acid to be detected 10. For example, the immobilizing unit is provided at least partly with oligonucleotides having the sequence B, which is at least partly complementary to a second subsection of the nucleic acid to be detected. By hybridization of the DNA sequences A and B with the nucleic acid to be detected 10 now the absorbers 1 may be immobilized at a specific location in the reaction solution and/or of the reaction vessel, in particular at the immobilizing unit.

When using a sedimentation or immobilization it may be advantageous that the attenuators not necessarily have to change their "homogeneous" attenuator properties (i.e., the attenuator properties they have as long as they are dispersed homogeneously or relatively homogeneous in the reaction solution), if the proximity to each other changes. For example, gold nanoparticles hardly change their attenuator properties if they are connected, however, their distance is reduced only moderately to some particle radii (e.g., the distance is about 5× particle radius) and they remain still (homogeneously) dissolved in the reaction volume. However, in case this connection results in a sedimentation of the nanoparticles, their attenuator properties for the fluorophors homogeneously remaining in the reaction solution may nevertheless have largely changed.

By a hybridization of the at least one functionalizing unit 4 of an absorber 1 with the functionalizing unit 6 of the immobilization unit or the reaction vessel R, in particular by the nucleic acid to be detected 10, the absorber 1 may be immobilized at the reaction vessel. Preferably, an absorber 1 may be bound to each functionalizing unit 6 of the reaction vessel R or the immobilization unit, in particular by a nucleic acid 10. Preferably, an absorber 1 has a plurality of functionalizing units 4, by which the absorber 1 may also simultaneously bind to a plurality of functionalizing units 6 of the immobilization unit or the reaction vessel R.

In case at least a part of the absorber 1 present in the solution is bound to the immobilization unit or the reaction vessel R, for example, in other parts of the solution the average concentration of absorbers 1 may be lower compared to the case when no absorber 1 is bound to the reaction vessel R. For example, this may result in that the transmissibility or the transparency of the solution for excitation light and/or of emission light in at least a partial volume of the solution, wherein the average concentration of absorbers 1 is lower, is greater than in a partial volume of the solution having a higher concentration of absorbers 1.

Alternatively or additionally this may result in that the distance of the surfaces of the nanoparticles 2 of the absorbers 1 connected to each other is so small, for example, smaller than 30 nm, such that a red shift of the extinction spectrum of the connected nanoparticles 2 occurs at least partly.

Alternatively or additionally also the dyes 8 may be immobilized by the nucleic acid 10 at a specific location in the solution, like, for example, at the bottom or a wall of the reaction vessel R. In this case, the attenuators 1 may remain homogeneously distributed in the solution or alternatively may also be immobilized at a specific location, preferably at a different location than the dyes 8, in the reaction solution and/or the reaction vessel.

Preferably, in this context the excitation of the dye components 8b formed in the microparticle 8a and/or the emission of emission light by at least one dye component 8b formed in the microparticle 8a is attenuated by at least 10%, more preferably by at least 25%, still more preferably by at least 50% and particularly preferable by at least 80%.

In contrast to methods known in the prior art, which, for example, are based on quenching and/or FRET, in the method according to the present invention a dye 8 may be influenced by a plurality of absorbers 1. This is not possible or only hardly possible in conventional methods based on quenching and/or FRET, in particular since within a Förster radius around a dye typically only a few acceptors or quenchers may be located and the same also must have a precise relative orientation to each other in order to effect a quenching process or a FRET energy transfer.

Since no microscopic interaction between dye and absorber is necessary, the excitation light and/or emission light of each dye is attenuated by a plurality of absorbers contained in the surrounding or adjacent solution. According to the present invention, a collective attenuation of the excitation light and/or emission light is effected by the optical density of the solution and not by the interaction of single absorbers with single dyes. Rather, the excitation light and/or the emission light of a major part (>50%) of all dyes is respectively attenuated by a plurality of absorbers, preferably by at least 5 absorbers, preferably at least 10 absorbers, particularly preferable at least 100 absorbers and particularly preferable at least 1000 absorbers. Each absorber typically attenuates the excitation light and/or emission light of a plurality of dyes.

According to a preferred embodiment of the present invention, for example, a plurality of absorbers 1 may be present in the solution and be, for example, homogenously dispersed in the solution. For a dye 8, which is, for example, present in the inner part of the solution, in contrast to dyes 8 present in the vicinity or directly at the boundary between the solution and the reaction vessel R, its optical excitation and/or the emission by this dye 8 is influenced by many absorbers 1, which are present between the dye 8 and the excitation light source and/or between the dye 8 and the detection unit for detecting the emission light.

If a dye 8 and an absorber 1, i.e. both photonically interacting partners, are freely or homogeneously dispersed in the solution (e.g., as a suspension, emulsion, dispersion), the average distance to the next partner may be roughly estimated as follows:

At first, it has to be determined, which of the two photonically interacting partners (absorber and dye) is present in a higher concentration in the solution. (If both partners have the same concentration, it may be assumed for determining the distances in the framework of the following instruction that one of the partners would have a higher concentration). In the following, the partner having the lower concentration is designated as "shortfall partner" and the partner having the higher concentration is designated as "excess partner". The average distance $\bar{D}$ in meters of specimen of the shortfall partner from each other is then estimated from its molar concentration [C] by using the following equation: $\bar{D}=(1000 \cdot NA \cdot [C])^{-1/3}$. In this context, NA is the Avogadro number.

The average distance of specimen of the excess partner to the most proximate shortfall partner $\overline{D_{\uparrow\downarrow}}$ in meters may then roughly be determined by the following equation:

$$\overline{D_{\uparrow\downarrow}} \approx \frac{\int_0^{\overline{D}/2} r \cdot 4\pi r^2 dr}{\int_n^{\overline{D}/2} 4\pi r^2 dr} = \frac{3}{8}\overline{D},$$

wherein it is assumed that a sphere having the radius $\overline{D}/2$ is put around each shortfall partner, which is homogenously filled with specimen of the excess partner. For practical purposes, the estimation $$\overline{D_{\uparrow\downarrow}} \approx \frac{3}{8}\overline{D}$$

is sufficient.

For example, in case dye molecules 8 having a concentration of 100 nM are used and e.g. gold nanoparticles 2 are used as absorbers 1 having a concentration of 100 pM, then the absorbers 1 or nanoparticles 2 form the shortfall partner. The average distance of the absorbers 1 among each other, i.e., the average distance between the center points of two nanoparticles 2 then results in $\overline{D}=2.55$ μm. The average distance of the dye molecules 8, i.e. of the excess partner, to the most proximate absorber 1 or nanoparticle 2 is then $$\overline{D_{\uparrow\downarrow}} = \frac{3}{8} \cdot 2.55 \text{ μm} \approx 1 \text{ μm}.$$

Particularly preferable the arithmetic average of the distance of the excess partner to the most proximate shortfall partner $\overline{D_{\uparrow\downarrow}}$ is preferably more than 10 nm, more preferably more than 50 nm, still more preferably more than 250 nm, more preferably more than 500 nm, still more preferably more than 1 μm, still more preferably more than 2 μm and in particular more than 5 μm. This applies preferably in case both partners are present in solution.

Although also the distance between a dye 8 and one of the influencing absorbers 1 may change by the presence of a nucleic acid to be detected, it is, however, preferably not necessary that the distance between the dye 8 and the absorber 1 changes, in particular on a nanometer scale, which is required, for example, in conventional methods based on quenching and/or FRET. In conventional methods the properties of the attenuators used therein often change with a $r^6$ dependency (wherein r is the distance between the center point of a dye and the center point of an attenuator). Thus, in such conventional methods measurable changes of the intensity of the emission light often occur only after the dye and the attenuator approximate to less than e.g. 30 nm or even less than 20 nm or even less than 10 nm.

Changes of the intensity of the emission light may occur in particular in that absorbers exit from the optical path of the excitation light and/or the emission light by sedimentation and/or immobilization. Alternatively or additionally, changes of the intensity of the emission light may occur in particular by an aggregation of absorbers with each other, like, for example, by forming dimers of absorbers. For this reason, for example, in preferred embodiments of the method according to the present invention the average distance between absorbers and dye may change, since the absorbers may, for example, accumulate in specific partial volumes of the solution (by sedimentation and/or immobilization) and/or the effective concentration of the absorbers in the solution changes (like, for example, by the formation of dimers, according to which two absorbers connect to one absorber unit). Such changes of the average distance between absorber and dye, however, typically occur on a micrometer or even millimeter scale. I.e., the average distance between absorber and dye (between their center points or centers of gravity) is preferably more than 30 nm before the reaction for detecting the nucleic acid and more than 100 nm after the reaction for detecting the nucleic acid, particularly preferable more than 50 nm before the reaction for detecting the nucleic acid and more than 1000 nm after the reaction for detecting the nucleic acid. Particularly preferable the average distance before and after the reaction for detecting the nucleic acid is always more than 100 nm. It is of particular importance that neither before nor after the reaction between absorber and nucleic acid for detecting the nucleic acid the average distance between absorber and dye is smaller or equal to the Förster radius in order to effect or elicit a change of the intensity of the emission light.

In case both absorber and dye are present as a dispersion/suspension before and after the reaction for detecting the nucleic acid, the average distance between absorber and dye is determined by the instruction for calculating $\overline{D_{\uparrow\downarrow}}$.

If either absorber or dye are not present in a dispersed or suspended state anymore after the reaction for detecting the nucleic acid (but, for example, immobilized, sedimented or removed otherwise), at first the average distance of absorber and dye before the reaction for detecting the nucleic acid is calculated according to the instruction for calculating and after the reaction for detecting the nucleic acid by an estimation of the average distance of absorber and dye from the geometry of the sample vessel.

In the above example with a dye concentration of 100 nM (in the form of a dye molecule) and a concentration of the absorber of 100 pM (nanoparticles), the average distance of the excess partner (dye) to the most proximate shortfall partner (here: nanoparticles) $\overline{D_{\uparrow\downarrow}}$ is in the range of one micrometer, as long as both partners are present in solution. According to the present invention, it may be intended to effect an aggregation and/or a precipitation of the absorber (here: the nanoparticles) by the detection of the nucleic acid. If, for example, all nanoparticles are precipitated and are then present at the bottom of the reaction vessel, by this reaction the average distance of the dyes (which are still present as a dispersion) to the absorbers (which are now precipitated) may as a consequence—depending on the size of the reaction vessel—typically rise to several millimeters.

In case either the absorbers 1 or the dyes 8 are strongly connected with the reaction vessel R or are immobilized at the same or lie on the bottom of the vessel by precipitation or gravity or sedimentation, the average distance of the freely suspended/dispersed partner to the most proximate bound or immobilized or precipitated partner may be estimated from the geometry of the reaction vessel 1 (in that the weighted average of how many particles in the solution volume are how far away from the boundary or the boundaries, on which the bound/immobilized/precipitated partner is present, is formed).

If the reaction vessel R is, for example, cylindrical (e.g., having a height of 6 mm), and after the reaction for detecting the nucleic acid one of the partners (e.g., the nanoparticles) has, for example, precipitated, i.e., is uniformly present as a sedimentation on the bottom of the vertically placed cylinder, while the other partner (e.g., the dye molecules) is present freely in the solution as a dispersion (which has a filling height of 6 mm), the average distance would then be 3 mm.

For example, the reaction vessel R may be a multiwell plate or a reaction tube (PCR tube) or an other closed or sealable or open reaction chamber.

Figures 1, 1B, 2:
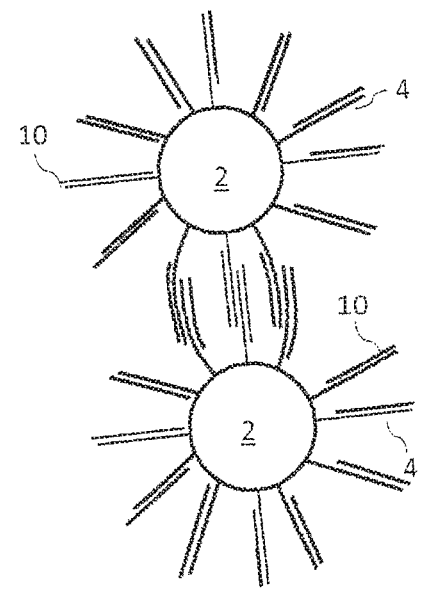
Figure 1D:
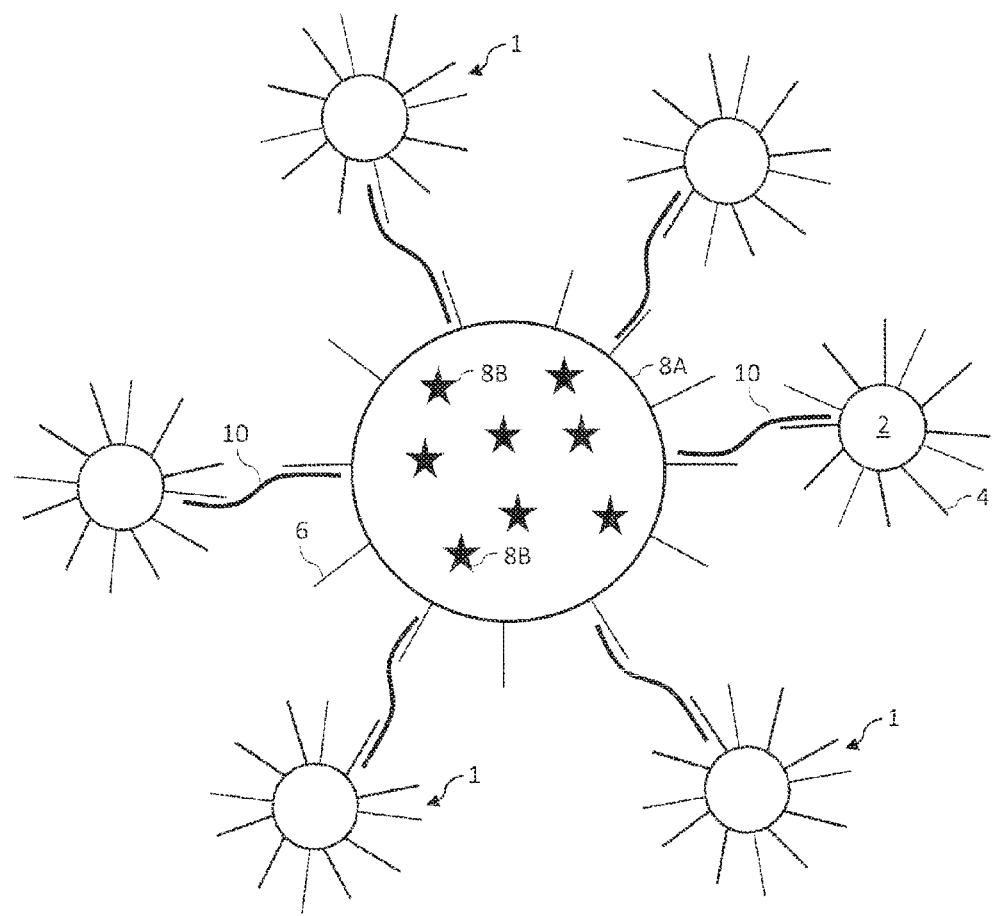

According to a third preferred embodiment, which is shown in FIG. 1D, also a dye 8 may serve as immobilizing unit, to which one or more absorber(s) 1, in particular via a nucleic acid 10, may be bound. For example, the dye 8 may comprise a fluorophore, which comprises a microparticle 8a or a bead, at which and/or in which at least one dye component 8b is attached and/or formed. For example, the microparticle 8a may be a spherule of polystyrene comprising at least one dye component 8b, like, for example, a fluorescing nanoparticle and/or at least one dye molecule. In this context, the dye components 8B may be integrated in the microparticle and/or be bound at its surface. If the dye components 8b are integrated in the microparticle 8a, it is advantageous that the microparticle 8a is at least partly transparent or at least partly transmissible for the excitation light and the emission light of the at least one dye component 8b integrated therein.

If at least one absorber 1, which may at least partly absorb the excitation light, is immobilized at the microparticle 8a, this may result in an attenuation or shielding of absorption light, such that less excitation light reaches the dye components 8b formed in the microparticle 8a as in the case that no absorber is immobilized at the microparticle 8a, and result in a reduction and/or prevention of the optical excitation(s) of the dye components 8b.

Alternatively or additionally the at least one absorber may be formed such that the at least one absorber 1 may absorb the emission light of the dye component 8b. In this case, the absorber 1 immobilized at the microparticle 8a may absorb the emission light of the dye component 8b, such that at least one dye component 8b in or at the microparticle 8a is at least partly shielded and/or attenuated and/or reduced by the absorber 1 bound to the microparticle 8a.

The binding of absorbers 1 to the microparticle 8a may, for example, be effected in that the functionalizing unit 4 of the absorber 1 is at least partly complementary to a first sequence section of the nucleic acid 10 and in that the functionalizing unit 6 of the dye is at least partly complementary to a second sequence section of the nucleic acid 10. In other words, the absorber 1 and the microparticle 8a may be formed such that the absorber 1 may be bound to respectively at least one functionalizing unit 6 of the microparticle 8a via the nucleic acid 10 to be detected.

For example, the fluorophore or dye 8 may comprise at least one fluorescing bead, like, for example, of polystyrene, wherein the bead is provided with at least two DNA oligonucleotides having the sequence A as functionalizing units 6, which is at least partly complementary to a sequence section of the nucleic acid to be detected. The absorbers 1 are provided, for example, with at least one DNA oligonucleotide having the sequence B as functionalizing unit 4, which is at least partly complementary to a second sequence section of the nucleic acid to be detected. By hybridizing the DNA sequences A and B with the nucleic acid to be detected, at least two attenuators may be brought in the vicinity of the fluorescing beads or may be immobilized at this location and thus may envelop the bead or microparticle 8. In this manner, the absorbers 1 may change the optical excitation of the dye components 8b in the bead and/or the emission by the dye components 8b in the bead in a particular efficient manner.

The average distance between the surface of the microparticle 8c or bead and the surface of an absorber 1 bound thereto may be e.g. larger than 10 nm and thus be larger than typical distances which would be necessary for a conventional interaction of a dye with a quencher or another dye based on quenching or FRET. In particular, the distance between the bead and an absorber 1 bound thereto may be larger than the FRET radius of a dye molecule optionally formed in the bead. In particular, the distance between a dye molecule optionally formed in the bead and an absorber 1 bound to the bead may be larger than the FRET radius of a dye molecule optionally formed in the bead.

Preferably, different beads or microparticles 8a having different dye components 8b and different DNA sequences as functionalizing units 6 may be used in a solution for a multiplexing, i.e. for the detection of several different nucleic acids in one reaction solution.

In this context, it may be sufficient that a single attenuator 1 merely has a weak attenuation effect on the irradiated excitation light and/or the emitted emission light, such that the attenuation of the excitation light and/or the emission light is preferably effected by at least two absorbers 1, more preferably at least 10 absorbers 1, still more preferably at least 100 absorbers 1, particularly preferably at least 1000 absorbers 1, in particular at least 10000 absorbers 1.

Oligonucleotides or nucleic acids may be attached to dyes 8 and/or attenuators 1 e.g. in the following manner: with a thiol bond, with a streptavidin-biotin bond, with ZNA or other cationic modifications; furthermore, passive sequences, like, for example, spacers or non-basic modifications like Spacer9, dSpacer, polyethylene glycols, may be present between the active recognition sequence and the attenuator or dye surface.

Figure 2B:
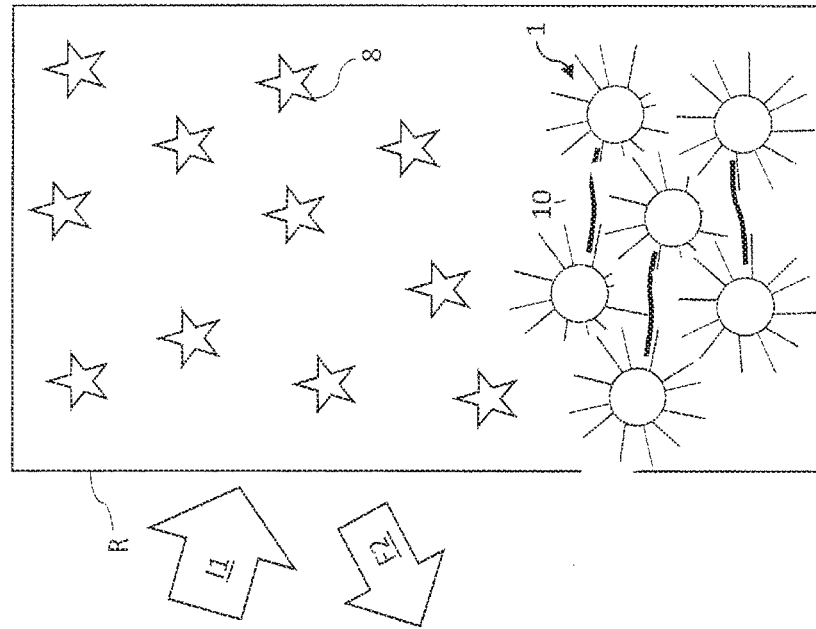
FIGS. 2A and 2B a schematic representation of the principle of operation of the method according to a preferred embodiment.
Figure 2A:
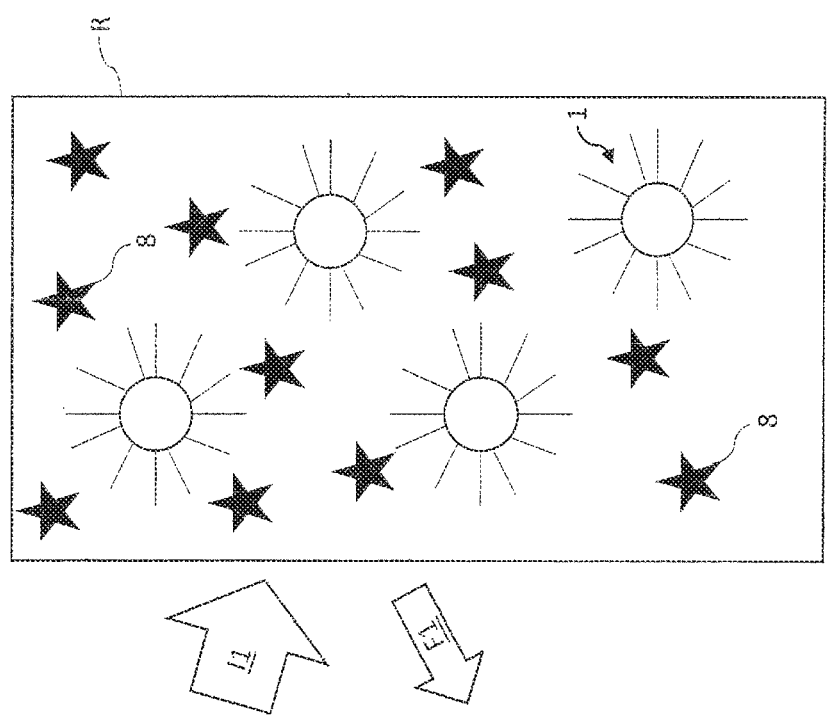

FIGS. 2A and 2B show a schematic representation of a method according to the present invention in a further preferred embodiment, wherein dyes 8 and absorbers 1 with nanoparticles 2 are present in the solution, an excitation light having the intensity I1 is irradiated and an intensity of the emission light F1 or F2 of at least a part of the dyes 8 is measured. Preferably, the absorption spectra of the absorbers 1 and the excitation spectra of the dyes 8 overlap at least partly with each other and with the spectrum of the excitation light. Furthermore, the absorption spectra of the absorbers 1 preferably overlap at least partly with the spectrum of the emission light of the dyes 8.

If, as shown in FIG. 2A, the absorbers 1 or the nanoparticles 2 are not aggregated, the absorbers 1 or the nanoparticles 2 absorb at least partly the excitation light, which is irradiated with the intensity I1, in an efficient manner. Preferably, in this manner the absorbers 1 shield the dyes 8 at least partly from the incident irradiation light in a particularly efficient manner.

Alternatively or additionally the absorbers 1 preferably shield the emission light emitted by the dyes 8, which is, for example, caused by a fluorescence of the dyes 8. In this manner, the emission light exiting the solution with the intensity F1 may be at least partly attenuated or completely suppressed. Preferably, the ratio of the intensity of the incident light I1 and the intensity of the emission light F1 exiting the solution is a measure for the attenuation of the excitation light and/or the emission light by the absorbers 1 and/or for the absorption spectrum of the absorbers 1 and/or for the average distance between the absorbers 1 and/or for their aggregation and thus a measure for the concentration or the presence of a nucleic acid to be detected 10 in the solution.

FIG. 2B shows a schematic representation of the case, wherein additionally at least one nucleic acid to be detected 10 is present in the solution of FIG. 2A, which may bind to the absorbers 1. In case the nucleic acid 10 hybridizes at least partly with the absorbers 1, the average distance between the absorbers 1 may reduce at least partly. This may result at least partly to an aggregation and/or a precipitation and/or a sedimentation of the absorbers 1. Particularly preferable, this is accompanied by a shift and/or broadening of the absorption spectrum of the plasmon resonance of the nanoparticles 2 of the absorbers 1, such that the absorption and/or extinction of the solution or the nanoparticles at the wavelength of the excitation light and/or the emission light at least partly changes. Preferably, this results in a smaller shielding of the dyes 8 from the incident light and/or to a smaller attenuation of the light emitted by the dyes 8. Particularly preferable, the absorbers 1, which are at least partly bound by the nucleic acid to be detected 10, aggregate and sediment at a specific location in the solution, like, for example, at the bottom of the reaction vessel R. In this manner, the transparency or transmissibility of at least a partial volume of the solution rises, since the concentration of absorbers 1 decreases locally in at least a part of the solution. In the case shown in FIG. 2B, for example, the transparency of the solution raises in an upper partial volume of the solution, since the absorbers 1 connected to the nucleic acid 10 at least partly sediment in a lower part of the solution. In this manner, the intensity F2 of the light emitted by the dyes 8, which exits the reaction vessel R, may be larger than the intensity of the emission light F1 in the case shown in FIG. 2A, even if the intensity I1 of the incident light is identical in both cases. Preferably, the ratio of the intensity of the excitation light I1 and the intensity of the emitted light F2 compared with the ratio of F1 to I1 is a measure for the attenuation of the excitation light and/or the emission light by the absorbers 1 and/or for the absorption spectrum of the absorbers 1 and/or for the average distance between the nanoparticles 2 and/or for their aggregation. Particularly preferable, a measure for a shift of the plasmon resonance of the nanoparticles 2 and/or for the average distance between the nanoparticles 2 and/or for their aggregation may be determined from a comparison and/or a difference and/or a quotient of the emitted light intensities F1 and F2 of the cases shown in FIGS. 2A and 2B particularly efficient and particularly precise, which is a measure for the presence or concentration of the nucleic acid to be detected. Furthermore, in order to be able to consider optionally occurring variations of the intensity of the incident excitation light, it may be advantageous to further consider the intensity of the excitation light. For example, in case an excitation light having the intensity I1 is incident at a first measuring time point and an excitation light having the intensity I2 is incident at a second measuring time point, a comparison and/or a difference and/or a quotient of the quotients F1/I1 and F2/I2 may be advantageous.

FIG. 3A to 3D show extinction spectra of solutions including a plurality of absorbers 1, wherein the absorbers each include a nanoparticle 2.

FIG. 3A shows the extinction spectrum of a solution having absorbers 1, each having gold nanoparticles (BBI SOLUTIONS, Cardiff, UK) with a diameter of 60 nm, with a concentration of 40 pM. The extinction spectra shown are provided in arbitrary units, i.e. plotted merely quantitative against the wavelength. Each nanoparticle 2 has approximately 1000 nucleic acids or functionalizing units 4, which have been functionalized via a thiol bond to the surface of the nanoparticles. The nanoparticles are dissolved in phosphate buffer (3.9 mM phosphate, pH 7) with 0.1% Tween 20, 5 mM $MgCl_2$, 7.85 mM NaCl. The extinction spectrum (recorded with a VARIAN CARY 50 spectrometer in a quartz cuvette having an optical path of 3 mm) of a particle solution without adding nucleic acid 10 (solid line) shows a plasmon resonance with a resonance maximum at a wavelength of about 530 nm. Adding a nucleic acid 10, via which at least two absorbers 1 or nanoparticles 2 may bind to each other not immediately or indirectly, does not show a significant change of the extinction spectrum 5 minutes after adding (dotted line).

According to FIG. 3B a nucleic acid 10 was added, which is at least partly complementary to the functionalizing units 4 of the absorbers 1 (final concentration also 150 nM, same buffer system as according to FIG. 3A). In this context, already after 1 minute a relatively strong change of the extinction spectrum (broken line) occurs compared with the curve before adding the non-complementary nucleic acid 10 (solid line). After 5 minutes the change is still stronger (dotted line). The observable or measurable change of the extinction spectrum is typical for a shift of the plasmon resonance of the nanoparticles, which may be a hint with regard to a smaller average distance of the nanoparticles 2 to each other, which is caused by the direct and/or indirect binding of the nanoparticles 2.

According to the present invention this effect may be used, for example, to effect a shift of the absorption spectrum of the absorbers 1 relative to the spectrum of the excitation light and/or the emission light. In case, for example, the excitation light is selected to have a wavelength of 470 nm and a dye having an absorption wavelength of 470 nm and an emission wavelength of 530 nm is used, like, for example, fluorescein, a significant change of the transparency of the solution for the excitation light and/or the emission light may be achieved by the binding of absorbers 1 and a shift of the extinction spectrum of the absorbers 1.

Particularly preferable, a combination of absorbers 1 and dyes 8 is selected such that the absorption of the absorbers 1 changes both at the excitation wavelength and at the emission wavelength, since this has a larger influence on the resulting intensity of emission light exiting the solution, as if only the absorption light wavelength or the emission light wavelength is influenced by a change of the absorption of the absorber and/or an aggregation of the absorber.

According to FIG. 3C the temperature of the solution of FIG. 3B is firstly raised to 60° C. (the extinction spectrum is shown as a dashed line). In this context, the change of the optical properties, in particular the extinction remains for the time being (strongly broadened and red-shifted or only weak plasmon resonance compared to the extinction spectrum of a sample without complementary nucleic acid). In case the sample temperature is further raised to 70° C., the extinction spectrum, however, essentially changes to return to the original state with a plasmon resonance maximum at a wavelength of about 530 nm (the extinction spectrum is shown as a solid line). This may be explained by the fact that the denaturing temperature of the DNA double strand having the sequence 1 and 7 (see the annex) is reached and that this double strand is separated. As a consequence, the bound absorbers 1 may again dislodge from each other, whereby the absorbers 1 are set free again, wherein the distance between the nanoparticles 2 or the absorbers 1 enlarges again, for example, by diffusion and/or by coulomb repulsion of the nanoparticles 2. This shows that the measurable change may also be reversible, if the binding of absorbers 1 to each other is released again.

According to FIG. 3D the nucleic acid 10, which was also used for recording the spectra of FIG. 3B, was added to other absorbers, which cannot bind via said nucleic acid. Also in this case no significant change may be observed, since the sequences of the functionalizing units 4 of the absorbers 1 again have a very small complementarity to the nucleic acid 10.

Figure 3E:
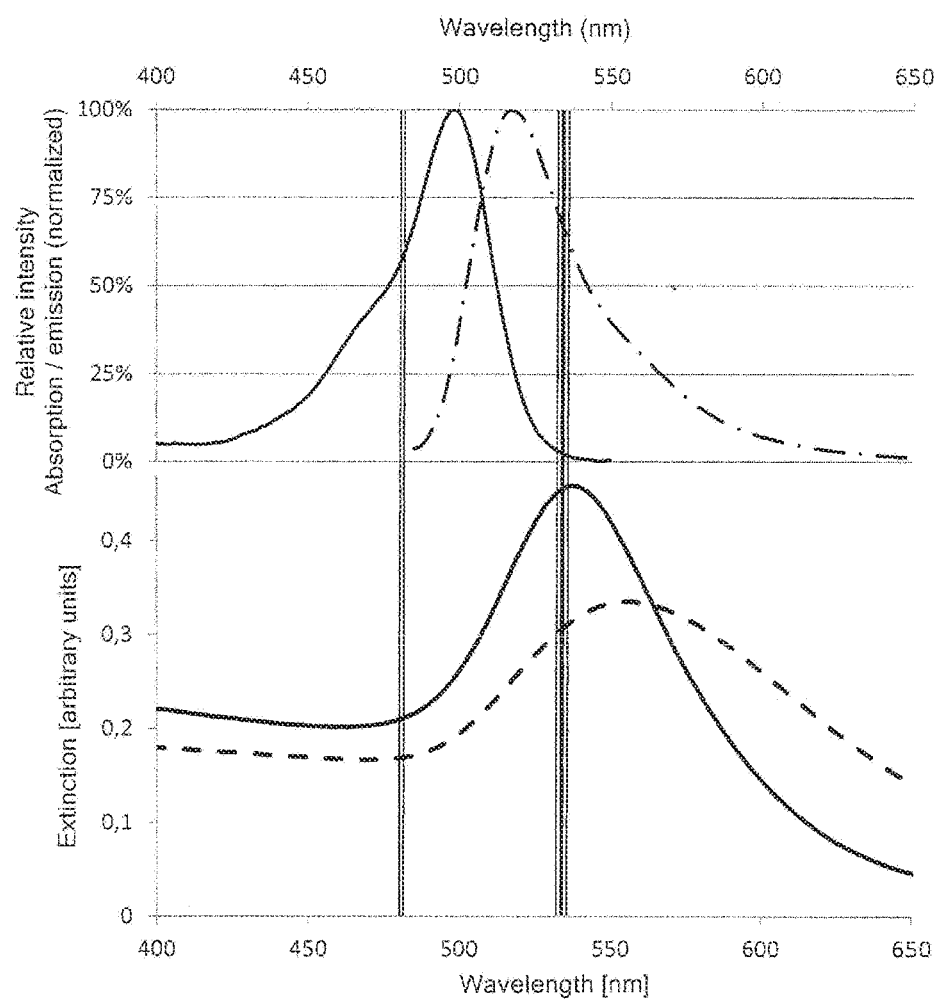

In the lower section FIG. 3E shows extinction spectra of absorbers 1 comprising spherical gold nanoparticles having a diameter of 60 nm. The solid line shows the extinction of these absorbers, in case the same are not bound and/or aggregated and/or sedimented with other absorbers 1, in particular via the nucleic acid 10. The dashed line illustrates the spectrum of the same or similar absorbers in case the same are bound with other absorbers. Due to the plasmonic interaction a red shift of the plasmon resonance absorption occurs, such that the maximum of the absorption spectrum is shifted to longer wavelengths and also has a lower optical density or a lower absorption coefficient or a lower extinction coefficient compared to the solid line. Further, it may be recognized that the bound absorbers 1 have a lower optical density or absorption coefficient also at shorter wavelengths, like, for example, between 400 and 500 nm, as the non-bound absorbers.

In the upper section of FIG. 3E the absorption spectrum or the excitation spectrum of the dye fluorescein (dotted line) as well as its emission spectrum (dashed-dotted-line) are shown for comparative purposes.

The vertical bars extending over the upper and the lower part of FIG. 3E designate the preferred wavelength of the excitation light at about 470 nm as well as the preferably detected or measured wavelength of the emission light at about 530 nm.

It can be seen in the shown comparison that a shift of the plasmon resonance, which occurs, for example, by a plasmonic interaction between the nanoparticles of the absorber, if the same have a small average distance, of, for example, 20 nm or less, significantly reduces the absorption of the excitation light and the emission light by the absorber 1. This means that a reduction of the distance between absorbers in the solution, in particular by their binding via a nucleic acid 10, results in a raised transparency of the solution for excitation light and emission light for or of fluorescein. For this reason, a combination of fluorescein as dye with absorbers comprising gold nanoparticles having a diameter of about 60 nm is particularly suitable for carrying out a method according to the present invention. In particular, this may have the advantage that the proposed combination may be used in conventional devices, which may be suitable, for example, for carrying out a PCR, like, for example, a LIGHTCYCLER, without being necessary to modify the same.

For example, absorber and dye may be adapted such that the excitation light and/or the emission light is/are absorbed or shielded efficiently, if the absorbers do not bind with each other and no shift of the absorption spectrum of the plasmon resonance occurs.

Alternatively, the absorber and the dye may be adapted such that the excitation light and/or the emission light is absorbed or shielded particularly efficient if and only if the absorbers bind with each other and a shift of the absorption spectrum of the plasmon resonance occurs. This may be achieved, for example, by a suitable selection of the excitation and emission spectrum of the dye as well as by the extinction properties of the absorber, for example, by a suitable selection of the size and/or the shape and/or the material of nanoparticles, which are comprised by the absorbers.

Furthermore, the functionalizing units 4 of the absorbers and/or the functionalizing units 6 of the immobilization means as well as an optionally used cationically modified nucleic acid may be adapted or selected such that, in particular in view of their nucleotide sequences, in case of the presence of the nucleic acid to be detected a binding and/or precipitation and/or immobilizing and/or sedimenting of the absorbers occurs and thus the transparency of the solution for excitation light and/or emission light is changed.

Alternatively, the functionalizing units 4 of the absorbers and/or the functionalizing units 6 of the immobilization means as well as an optionally used cationically modified nucleic acid may be adapted or selected such that, in particular in view of their nucleotide sequences, in case of the absence of the nucleic acid to be detected or the presence of a small concentration of the nucleic acid to be detected below a detection limit, a binding and/or precipitation and/or immobilizing and/or sedimenting of the absorbers occurs and thus the transparency of the solution for excitation light and/or emission light is changed. This may, for example, be achieved in that the nucleic acid enters into a competition to other components in the solution and thus a binding of absorbers with each other does not occur or occurs only in a smaller amount.

FIG. 4A to 4C-2 show schematic representations of effects of preferred embodiments of the method according to the present invention.

Figure 4A:
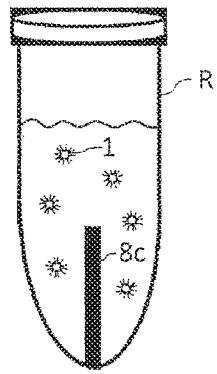

In a first preferred embodiment shown in FIG. 4A a plurality of dyes 8 is formed in a dye device 8*c*. According to the present embodiment the dye device 8*c* has the shape of a rod or a spike and extends away from the reaction vessel into the solution, which is present in the reaction vessel. The dye device 8*c* may be a part of the reaction vessel R and/or connected therewith. In this context, the dye device 8*c* is at least partly surrounded by the solution, in particular fully surrounded by the solution and/or the reaction vessel R.

The dye device 8*c* is provided with dyes 8, i.e. dyes 8 are formed in and/or at the dye device 8*c* and/or the dye device 8*c* itself comprises luminescent or fluorescent material. According to the preferred embodiment in FIG. 4A, it is not required that additional dyes 8 are present in the solution, although this is possible.

In case the absorbers 1 are dispersed essentially uniform in the solution in the reaction vessel R, this may result in an efficient shielding of the dyes 8 present in the dye device 8*c* from excitation light and also an efficient shielding of the emission light. In case the presence of the nucleic acid to be detected 10 results in a shift of the plasmon resonance and/or in a sedimentation or precipitation of the absorbers 1 from the solution, this may result in a reduction of the attenuation, such that a larger intensity of the emission light exits the solution or the reaction vessel. In this manner, for example, a detection of the nucleic acid to be detected in the solution may be carried out with particular efficiency by measuring the intensity of the emission light.

Figures 1, 4B:
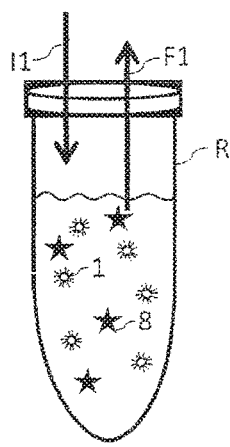
Figures 2, 4B:
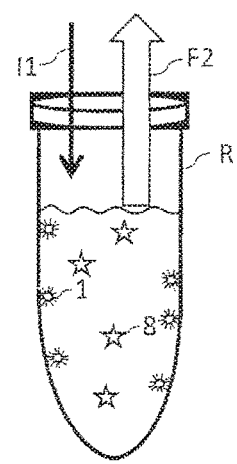

FIGS. 4B-1 and 4B-2 show a further preferred embodiment, wherein a plurality of dyes 8 and absorbers 1 are present in the solution. In this case, the walls of the reaction vessel R are at least partly provided with functionalizing units 6, while in particular the bottom and/or the lid is/are not provided with functionalizing units 6. FIG. 4B-1 shows the case that no nucleic acid to be detected 10 or a non-detectable amount of nucleic acid 10 is present in the solution. In this case, both the absorbers 1 and the dyes 8 are dispersed essentially homogeneous in the solution. Thus, excitation light and/or emission light essentially in the whole volume of the solution is at least partly efficiently absorbed or shielded by the absorber. This results in that the intensity F1 is low or lower than in a case, wherein the absorber is not homogeneously dispersed in the solution.

FIG. 4B-2 shows the case, wherein a measureable concentration of nucleic acid 10 is present in the solution. This results in that the absorber hybridizes at least partly with the functionalizing units 6, which are attached to the wall of the reaction vessel R and are immobilized at the wall of the reaction vessel R. This results in that at the corresponding boundaries between the solution and the reaction vessel R the concentration or density of the absorbers 1 rises, whereas the density or concentration in other partial volumes of the solution decreases, in particular in partial volumes, which are distant from the boundary, i.e. which are closer to the center point of the solution volume.

In case, for example, the excitation light is irradiated through the lid, for example, along a vertical central axis of the reaction vessel R, and the emission light exiting through the lid of the reaction vessel R is detected, in case that the nucleic acid to be detected is present in the solution, a higher intensity of emission light may arise, which propagates through the lid out of the reaction vessel, as if no nucleic acid to be detected 10 is present in the solution (FIG. 4-B1). Since the excitation light is irradiated into the solution from above, i.e. in particular through the lid, and the emission light, which exits the solution in particular upwardly through the lid, is measured, the measured intensity F2 is larger than the intensity F1 (FIG. 4B-1), since the concentration of the absorbers 1 in the vertical direction distant from the wall of the reaction vessel R is lower than in case of FIG. 4B-1.

Figures 1, 4C:
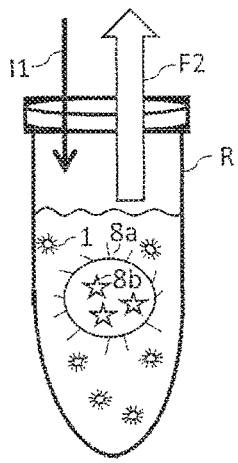
Figures 2, 4C:
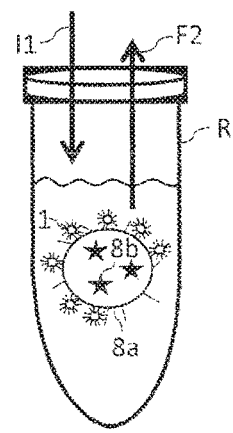

FIGS. 4C-1 and 4C-2 show a further preferred embodiment, wherein a plurality of dyes 8 is present in the form of microparticles 8a, which in turn are provided with dye components 8b. In case no nucleic acid to be detected 10 is present in the solution (FIG. 4-C1), no absorbers 1, which are present in the solution, may bind at the microparticle and thus remain dispersed essentially homogeneous in the solution. In case a nucleic acid to be detected 10 is present in the solution, the absorbers 10 may bind at least partly to the functionalizing units 6a of the microparticles 8a via the nucleic acid to be detected 10. Thus, similar to the first preferred embodiments shown in FIG. 1D, the dyes 8 or the dye components 8b in the respective microparticles 8a are shielded from the irradiated excitation light. This in turn results in a decrease of the optical excitations of the dye components 8b and thus in a decrease of the intensity of the emission light, which may be measured outside the reaction vessel. Furthermore, as in the other preferred embodiments (in particular FIG. 4A to 4B-2), the absorbers 1 may be formed such that also the remaining emission light, which is emitted despite the shielding of excitation light by the microparticle 8a or by the dyes 8, may be absorbed or attenuated. Thus, in the presence of nucleic acids 10, there results an intensity of the emission light F2 lower than the intensity F1 of the emission light in the absence of the nucleic acid to be detected 10.

The present invention is further explained by the following examples, however, is not restricted to the following examples.

Example 1: Real-Time PCR with Nanoparticles and Cationically Modified Nucleic Acid (ZNA) with Background Dye Dissolved in the Solution The real-time PCR reaction discussed in this example was carried out in a ROCHE LIGHT CYCLER 1.5 with the software version 4.1.1.21 in plastic capillaries of the manufacturer GENAXXON BIOSCIENCE GMBH.

A polymerase chain reaction was carried out for an indirect detection of a nucleic acid. The used primer system consists of a modified forward primer oligonucleotide having the sequence 1 (see the annex), which was functionalized on gold nanoparticles, and a reverse primer having the sequence 2 with a cationic modification. The sequences referred to in this example are shown in the annex.

In this context, the cationically modified primer preferably comprises a cationically modified nucleic acid. This is a nucleic acid having a cationic block or a cationic section. The same may be, for example, a nucleic acid having a cationic extension at least at one end. The cationic extension preferably has an average charge density which is less anionic than the average charge density of a nucleic acid, in particular if both the nucleic acid and the cationic extension are present in the surrounding typically for the nucleic acid. In other words, the cationic extension is preferably electrically charged more positively than a nucleic acid. The nucleic acid having a cationic modification or the cationically modified nucleic acid preferably further comprises a section or a hybridization section predominantly comprising a nucleic acid and a cationic extension conjugated thereto.

In a preferred embodiment the cationic extension of the cationically modified nucleic acid comprises cationic spermines. In this case, the cationic extension comprises between 1 and 20 spermines, preferably between 2 and 15 spermines, particularly preferable between 2 and 10 spermines, in particular between 2 and 5 spermines. The average electrical charge density of a cationically modified nucleic acid is less anionic than the average electrical charge density of a non-cationically modified nucleic acid. In this manner, for example, the electrostatic repulsion between a cationically modified nucleic acid and a non-cationically modified nucleic acid is smaller than the electrostatic repulsion between two non-cationically modified nucleic acids. Particularly preferable a cationically modified nucleic acid and a non-cationically modified nucleic acid attract each other electrostatically.

For example, a cationically modified nucleic acid comprises a nucleic acid of the type of a ZIP NUCLEIC ACID (ZNA) of the manufacturer METABION (METABION INTERNATIONAL AG, Planegg, Germany), which is described, for example, in document WO 2007 069 092 B1 or WO 2009 083 763 A1. Alternatively or additionally, a cationically modified nucleic acid may comprise at least one cationically charged dye and/or other cationic units. Adding at least one cationic unit to a nucleic acid is preferably effected at the 5' terminus and/or at the 3' terminus of the nucleic acid.

The modified primer oligonucleotide having the sequence 1, which is functionalized to the nanoparticle, includes sequence 3 as a subsequence (this sequence serves as the actual primer sequence, additionally a subsequence of 35 adenine bases, which serve as a spacer between the nanoparticle surface and the primer subsequence, additionally two non-basic modifications Spacer9 between the distance subsequence and the primer subsequence, which prevents the transcription of the distance subsequence by the polymerase (see, for example, patent application DE 102013215168.3), furthermore, the modified primer oligonucleotide having the sequence 1 contains a thiol modification at the 5' terminus, by which the oligonucleotide is bound on the surface of gold nanoparticles. The gold nanoparticles having a diameter of 60 nm (provided by BBI Solutions)

each carry about 1000 oligonucleotides having the sequence 1. The thus functionalized nanoparticles serve as an absorber.

The reverse primer having the sequence 2 carries a cationic modification having three cationic units (ZNA3) at the 5' terminus. In this case, the cationic modification is attached to the 5' terminus of the primer and not at the 3' terminus, in order not to prevent the elongation by the polymerase, which starts at the 3' terminus of the primer. The nucleic acid having the sequence 4 is amplified. Dissolved fluorescein is used as the fluorophore (as fluorescein sodium salt F6377, purchased from Sigma Aldrich and initially dissolved in water). Each reaction consists of 9 µl Mastermix and 1 µl nucleic acid solution or water. 9 µl Mastermix for one reaction are composed as follows:

TABLE 1

| | Stock concentration | Final concentration in 10 µl | µl for 1 reaction |
|---|---|---|---|
| Water | | | 1 |
| 5x Apta Tag Genotyping Master (Roche) [x-times] | 5 | 1 | 2 |
| Nanoparticle-oligonucleotide conjugate [pM]* | 200 | 40 | 2 |
| Reverse primer sequence 2 [nM] | 3000 | 300 | 1 |
| MgCl2 [mM] | 50 | 5 | 1 |
| Tween 20 (%) | 1 | 0.1 | 1 |
| Fluorescein (nM) | 1000 | 100 | 1 |

*the nanoparticle-oligonucleotide conjugates are functionalized (according to J. Hurst et al., Anal. Chem., 78(24), 8313-8318, 2006). After the functionalization and 6 washing steps the nanoparticle-oligonucleotide conjugates are present in a concentration of 200 pM in phosphate buffer (5 mM phosphate, pH 7) with 0.1% Tween 20, 10 mM NaCl.

The PCR protocol consists of 40 cycles of 5 seconds 90° C., 15 seconds 60° C. and 15 seconds 72° C. The signal detection is carried out after each 72° C. step.

Figure 5:
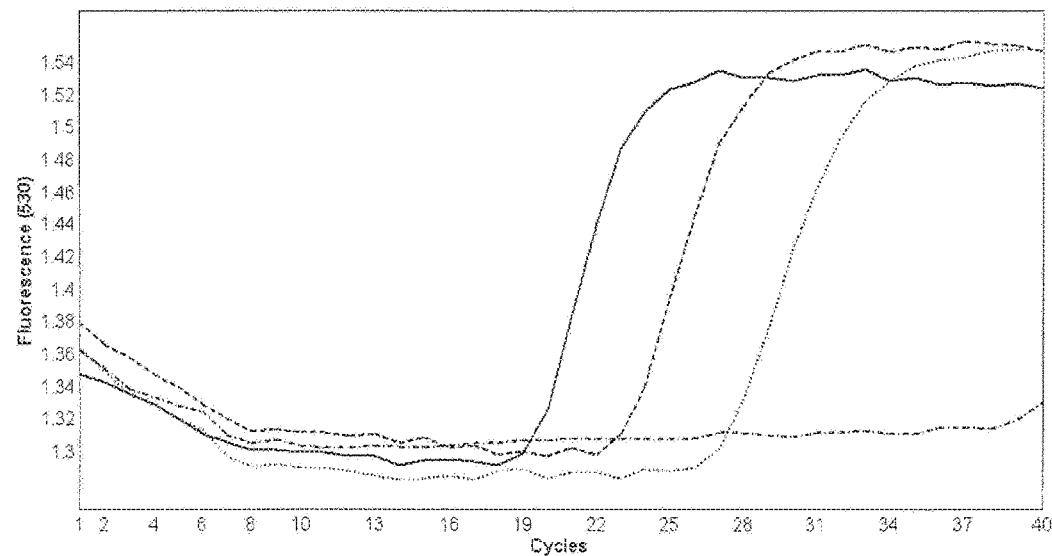
FIG. 5: Real-time PCR curves measured by a method according to the present invention according to the described example 1.

FIG. 5 shows several real-time PCR curves of the 530 nm fluorescence channel (in line with the emission wavelength of fluorescein) of three different starting concentrations of the nucleic acid having the sequence 4 (present as oligonucleotide) and a negative control without nucleic acid as target sequence. The curves in FIG. 5 essentially show a course typical for a real-time PCR:

Except a common decrease of the measured fluorescence the detected fluorescence remains virtually unchanged in the first 18 PCR cycles. In this case (depending on whether nucleic acid is contained as starting material in the sample or not) new DNA double strands are generated as amplicon in each cycle, however, in this case the amount is not yet sufficient to change the attenuator properties such that the fluorescence of the fluorophore is strongly changed. For the sample, wherein 1 µl of a 1 pM concentration of the nucleic acid having the sequence 4 (see the annex) was used as a starting material (solid line), the fluorescence strongly rises starting from about the 20. cycle to become saturated thereafter. This point of rise has a large explanatory power for the starting concentration of the nucleic acid having the sequence 4, since a sample having a 10 times lower starting concentration rises only until the 24. cycle (dashed line), for a 100 times lower starting concentration it rises only until the 27. cycle (dotted line). Without nucleic acid having the sequence 4 as the starting material no rise can be seen until the 38. cycle (dashed-dotted line).

The measureable change of the intensity of the emission light, which is detectable starting from a certain minimum concentration of amplicon or nucleic acid to be detected originates here from a cooperation of the unchanged fluorescence properties or the unchanged quantum yield of the fluorescein dye used in the solution and the changed attenuator properties of the absorber, when the absorbers connect with the nucleic acid to be detected or via the nucleic acid with the ZNA. In this case, the changed attenuator properties emerge as changed optical properties of the gold nanoparticles by a connection with a sufficiently larger number of oligonucleotides having a cationic modification (here: reverse primer as ZNA) and effect a change of the absorption of the excitation light and/or the emission light.

Since the oligonucleotides functionalized to the nanoparticles at least partly act as a primer and the ZNA oligonucleotides act as a reverse primer, replicated single strands with nanoparticles (or, in other words, primers elongated by the polymerase functionalized at nanoparticles) may hybridize at replicated single strands with ZNA (or, in other words, primers elongated by the polymerase having a cationic modification). In this case, a connection of nanoparticles with ZNA may result in a change of the electrostatic stabilization of such composites of nanoparticles and ZNA in solution, such that said composites at least partly precipitate from the solution and/or sediment at the bottom of the reaction vessel and thus the local concentration of absorbers decreases in other parts of the solution. Furthermore, due to the above, an aggregation of such composites, in particular of nanoparticles, may occur, wherein the plasmon resonance and thus the absorption spectrum changes due to a small average distance of these nanoparticles and/or the absorption efficiency diminishes. Thus, this may result in a larger local transmittance or transmissibility of the solution at the excitation wavelength and/or at the emission wavelength.

In the example as shown fluorescein was excited by the LIGHT CYCLER at a wavelength of 470 nm and then emitted emission light. In this context, the maximum of the fluorescence is at a wavelength of 530 nm, wherein in the selected mode in the LIGHT CYCLER the fluorescence may be measured particularly efficient.

The nanoparticles in the dissolved state without bonding to oligonucleotides having a cationic modification (i.e., for example, in the first cycles of the real-time PCR before the signal change) have an extinction maximum at a wavelength of about 530 nm and a still significant extinction at 470 nm. Thus, they re-absorb a significant part of the fluorescein emission at 530 nm and additionally reduce the excitation at 470 nm. The decreasing nanoparticle extinction in the sample both at 470 nm as well as at 530 nm by a connection of the gold nanoparticles with a sufficiently large number of oligonucleotides having a cationic modification now results in an increased fluorescence signal of the fluorescein and thus in a measurable change of the fluorophore signal due to a more effective excitation and a less disturbed emission with a lower re-absorption by the nanoparticles.

The concentration of the fluorescein may be selected, for example, also 10 times higher, such that both the basis level of the fluorescence signal as well as the absolute signal strength rise. At a significantly diminished concentration (final concentration of fluorescein of 10 nM) both the basic level of the fluorescence signal as well as the absolute signal strength are significantly diminished and it may happen that samples are not recognized by the instrument and the software in the so called "seek process" at the beginning of the real-time PCR.

Example 2: Real-Time PCR with Nanoparticles and with Dissolved Background Dye

For an indirect detection of a nucleic acid a linear polymerase chain reaction, i.e. with only one primer, was carried out. The used primer consists of a modified forward primer oligonucleotide having the sequence 5, which was functionalized on gold nanoparticles. The modified primer oligonucleotide having the sequence 5 includes a subsequence serving as actual primer sequence, additionally a distance subsequence of 35 adenine bases, which serves as a spacer between the nanoparticle surface and the primer subsequence, additionally two non-basic modifications Spacer9 between the distance subsequence and the primer subsequence, which prevents a transcription of the distance subsequence by the polymerase (see, for example, patent application DE 102013215168.3), furthermore, the modified primer oligonucleotide having the sequence 5 contains a thiol modification at the 5' terminus, by which the oligonucleotide is bound on the surface of gold nanoparticles. The gold nanoparticles having a diameter of 60 nm (provided by BBI Solutions) each carry about 1000 oligonucleotides having the sequence 5. The nanoparticles serve as an attenuator. The nucleic acid having the sequence 6 (see the annex) is amplified (strictly speaking, in this case no amplification takes place, but merely an elongation of the primer having the sequence 5 according to the specification of sequence 6, such that strands complementary to sequence 6 are generated at the nanoparticle). Dissolved fluorescein is used as the dye or fluorophore (as fluorescein sodium salt F6377, purchased from Sigma Aldrich and initially dissolved in water). Each reaction consists of 9 μl Mastermix and 1 μl nucleic acid solution or water. 9 μl Mastermix for one reaction are composed as shown in table 2:

TABLE 2

|  | Stock concentration | Final concentration in 10 μl | μl for 1 reaction |
|---|---|---|---|
| Water |  |  | 2 |
| 5x Apta Taq Genotyping Master (Roche) [x-times] | 5 | 1 | 2 |
| Nanoparticle-oligonucleotide conjugate [pM]* | 200 | 40 | 2 |
| MgCl2 [mM] | 200 | 20 | 1 |
| Tween 20 (%) | 1 | 0.1 | 1 |
| Fluorescein (μM) | 10 | 1 | 1 |

*the nanoparticle-oligonucleotide conjugates are functionalized (according to J. Hurst et al., Anal. Chem., 78(24), 8313-8318, 2006). After the functionalization and 6 washing steps the nanoparticle-oligonucleotide conjugates are present in a concentration of 200 pM in phosphate buffer (5 mM phosphate, pH 7) with 0.1% Tween 20, 10 mM NaCl.

The PCR protocol consists of 60 cycles of 5 seconds 90° C., 30 seconds 58° C. (in this case, elongation by polymerase and annealing of the primer were combined to one step). The signal detection is carried out after each 58° C. step.

Figure 6:
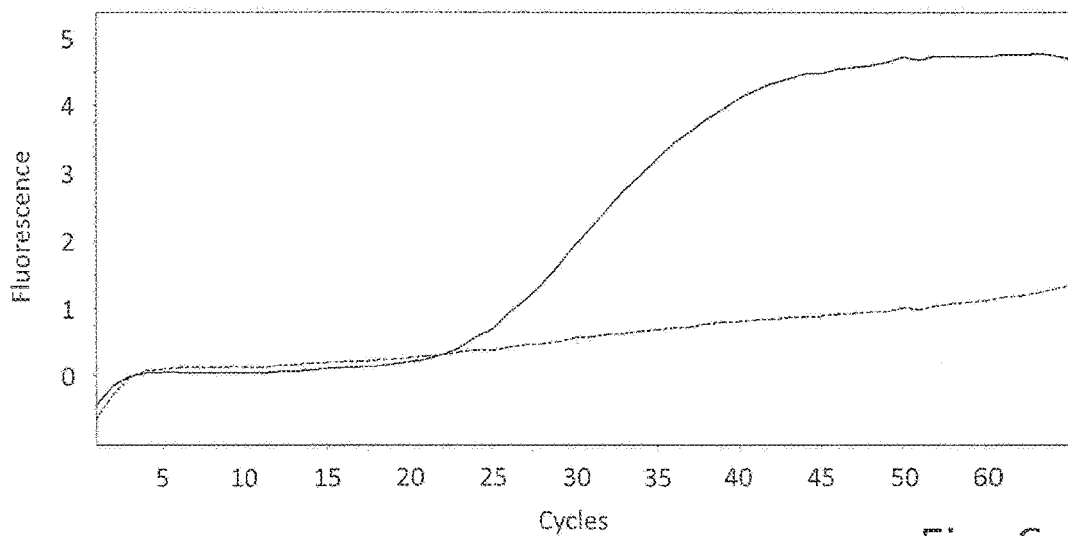
FIG. 6: Real-time PCR curves measured by a method according to the present invention according to the described example 2.

FIG. 6 shows real-time PCR curves of the 530 nm fluorescence channel (in line with the emission wavelength of fluorescein) of a sample with the nucleic acid having the sequence 6 (present as oligonucleotide) and a negative control without nucleic acid as target sequence. Also in this case, the curves essentially show a course typical for a real-time PCR: Except a common increase of the measured fluorescence in the first cycles the detected fluorescence remains virtually unchanged in the first 22 PCR cycles. In this case (depending on whether nucleic acid is contained as starting material in the sample or not), however, new primers having the sequence 5 are elongated according to the specification of sequence 6 also in each cycle, such that strands complementary to sequence 6 are generated at the nanoparticle, wherein, however, here the amount is not yet sufficient to change the attenuator properties such that the fluorescence of the fluorophore is strongly changed. The reason for the common increase in the first 3 cycles is not clear. For the sample, wherein 1 μl of a 10 nM concentration of the nucleic acid having the sequence 6 was used as a starting material (solid line), the fluorescence rises starting from about the 22. cycle to become saturated thereafter again. This point of rise has a large explanatory power for the presence of the nucleic acid having the sequence 6, since in the sample without nucleic acid having the sequence 6 as starting material no significant rise is visible until the 60. cycle (dotted line in FIG. 6).

The measureable change of the intensity of the fluorophore signal, which is detectable starting from a certain minimum concentration of amplicon or nucleic acid to be detected originates here from a cooperation of initially virtually unchanged fluorescence properties of the fluorescein dye used in the background of the solution and the changed absorber properties (here: the optical properties of the gold nanoparticles by a connection with each other due to a sufficiently large number of elongated primer oligonucleotides bound on the nanoparticles).

Fluorescein is excited by the LIGHT CYCLER at a wavelength of 470 nm and emits the maximum fluorescence at 530 nm, wherein in the selected mode of the LIGHT CYCLER also the fluorescence is measured. The nanoparticles in the dissolved state without bonding to each other (i.e., for example, in the first cycles of the real-time PCR before the signal change) have an extinction maximum at a wavelength of about 530 nm and a still significant extinction at 470 nm. Thus, they re-absorb a significant part of the fluorescence emission at 530 nm and additionally reduce the excitation at 470 nm. The decreasing nanoparticle extinction in the sample both at 470 nm and at 530 nm by the connection with each other due to a sufficiently large number of elongated primer oligonucleotides bound on the nanoparticles now results in an increased fluorescence signal of the dyes or the fluorescein and thus in a measurable change of the fluorophore signal due to a more effective excitation and a less disturbed emission by the dyes having less re-absorption by the nanoparticles.

Annex
Sequence listing (sequence progression each from 5' to 3':
Sequence 1:
(SEQ ID No. 1; SEQ ID No. 2)
5'Thiol-AAAAAAAAAAAAAAAAAAAAAAAAAAAAAAAAAAA/Sp9//S
p9/AGATGGTATGTGGAAGTTAGATTGG Sequence 2:
(SEQ ID No. 3)
Z3-CCTGGAATAATGACGCTATGA Sequence 3:
(SEQ ID No. 4)
AGATGGTATGTGGAAGTTAGATTGG Sequence 4:
(SEQ ID No. 5)
TCAATATGTATGCTTTGGTCTTTCTGCATTCCTGGAATAATGACGCTATG
ATCCCAATCTAACTTCCACATACCATCTTCTTT Sequence 5:
(SEQ ID No. 6; SEQ ID No. 7)
5'Thiol-AAAAAAAAAAAAAAAAAAAAAAAAAAAAAAAAAAA/Sp9//S
p9/GCAGAGCAAGGACTGATACA -continued Sequence 6:
(SEQ ID No. 8)
AATTTGTTCGCATCAAACGGAAAATCACCATCATGTGTCCTACTGATTGC

CAAGCTGTTGGATATTGTATCAGTCCTTGCTCTGCATGTA

Sequence 7:
(SEQ ID No. 9)
Z4-CCAATCTAACTTCGACAT

Z3 means three cationic units in the ZNA modification

/Sp9/ is a non-basic modification Spacer9

LISTING OF REFERENCE NUMERALS

1 Absorber
2 Nanoparticle
4 Functionalizing unit of an absorber
4a Oligonucleotide
6 Functionalizing unit of an immobilizing means
6a Oligonucleotide
8 Dye
8a Microparticle
8b Dye component
8c Dye device
10 Nucleic acid (to be detected)
11 Light source or laser
13 Sample holder
15 Windows or recesses
16 Sample
R Reaction vessel
I1 Intensity of incident excitation light
T1, T2 Intensity of transmitted light
F1, F2 Intensity of fluorescence radiation
Spectra
Extinction [arbitrary units]
Wavelength [nm]
60°
70°
Extinction [arbitrary units]
Wavelength [nm]
Extinction [arbitrary units]
Wavelength [nm]
Extinction [arbitrary units]
Wavelength [nm]
Extinction [arbitrary units]
Wavelength (nm)
Wavelength [nm]
Relative intensity
Absorption/emission (normalized)

The invention claimed is:

1. A method for detecting at least one nucleic acid to be detected in a solution, comprising the steps of:
providing at least one dye, wherein at least one of the solution and a reaction vessel containing the solution, comprises the dye and wherein the at least one dye is adapted to emit an emission light due to an optical excitation by an excitation light;
providing at least one absorber in the solution, wherein the at least one absorber is adapted to absorb at least one of the emission light and the excitation light to cause an attenuation of at least one of the emission light and the excitation light and wherein the attenuation is influenced by a bonding of the at least one absorber to the nucleic acid to be detected; and
detecting the nucleic acid to be detected by radiating the excitation light into the solution and measuring an intensity of the emission light, wherein a change of the measured intensity of the emission light correlates with the presence of the nucleic acid to be detected and wherein the change of the measured intensity of the emission light is influenced or caused by the binding of the at least one absorber to the nucleic acid to be detected;
wherein the attenuation of at least one of the emission light and the excitation light by the at least one absorber occurs independently of a quantum yield of the at least one dye.

2. The method according to claim 1, wherein measuring the intensity of the emission light is carried out by measuring the emission light immediately outside of the reaction vessel, wherein the solution is present, and wherein the excitation light and the emission light at least partly propagate(s) through the solution.

3. The method according to claim 1, wherein the at least one dye is a fluorophore and wherein the fluorophore is selected from the group consisting of a fluorescent dye, a fluorescent polymer, a fluorescent nanoparticle and a fluorescent microparticle.

4. The method according to claim 1, wherein a plurality of dyes is provided, which are essentially homogeneously dispersed in the solution.

5. The method according to claim 1, wherein a plurality of absorbers is provided.

6. The method according to claim 5, wherein at least a part of the plurality of absorbers is respectively functionalized with at least one functionalizing unit, wherein the functionalizing unit comprises a second nucleic acid.

7. The method according to claim 5, each of the plurality of absorbers being selected from the group consisting of a particle, a nanoparticle, a metallic nanoparticle, a microparticle, a pigment, and a dye molecule.

8. The method according to claim 6, wherein the at least one functionalizing unit is at least partly complementary to at least one first sequence section of the nucleic acid to be detected and is adapted to hybridize with a single strand of the nucleic acid to be detected.

9. The method according to claim 8, wherein the at least one dye is formed as a fluorescent microparticle, which is functionalized with at least two oligonucleotides, which are at least partly complementary to at least one second sequence section of the nucleic acid to be detected, wherein the second sequence section at least partially overlaps with the first sequence section.

10. The method according to claim 9, wherein at least one of the optical excitation of the dye and/or the emission of emission light by the dye is attenuated, if at least two absorbers, which are respectively functionalized with the at least one functionalizing unit, are bound and immobilized to the dye.

11. The method according to claim 10, wherein the at least two absorbers are bound to the dye via the nucleic acid to be detected.

12. The method according to claim 6, wherein each absorber functionalized with the at least one functionalizing unit is adapted for binding to at least one of a further absorber and the reaction vessel via the functionalizing unit by the nucleic acid to be detected.

13. The method according to claim 12, wherein binding of at least two of the plurality of absorbers causes sedimentation of the respective bound absorbers and wherein the sedimentation causes a change of the attenuation of at least one of the excitation light and the emission light by the absorber.

14. The method according to claim 12, wherein binding of at least two of the plurality of absorbers causes change in an absorption efficiency, of the at least two of the plurality of absorbers, for at least one of the excitation light and the emission light, and wherein the change of the absorption efficiency of the at least two of the plurality of absorbers causes a change of the attenuation of at least one of the excitation light and the emission light.

15. The method according to claim 12, wherein binding of an absorber of the plurality of absorbers with the reaction vessel causes an immobilization of the respective bound absorber and wherein the immobilization of the respective bound absorber causes a change of the attenuation of at least one of the excitation light and the emission light.

16. The method according to claim 6, the functionalizing unit comprising an oligonucleotide.

17. The method according to claim 1, wherein the detection of the nucleic acid to be detected is carried out in the solution during, after, or during and after an amplification or replication of the nucleic acid to be detected.

18. The method according to claim 17, wherein at least a part of the plurality of absorbers is respectively functionalized with a least one functionalizing unit, wherein the functionalizing unit is an oligonucleotide and the oligonucleotide at least partly serves as a primer.

19. The method according to claim 17, wherein the amplification or replication is carried out by a PCR.

20. The method according to claim 1, wherein the detection of the nucleic acid to be detected is carried out as part of real-time PCR.

21. A kit for detecting at least one nucleic acid to be detected in a solution, comprising:
at least one dye for introducing into the solution, wherein the at least one dye is adapted to emit emission light due to an optical excitation by excitation light; and
at least one absorber for introducing into the solution, wherein the absorber is adapted to absorb at least one of the emission light and the excitation light and to effect an attenuation of at least one of the emission light and the excitation light, and wherein the attenuation is influenced by a bonding of the at least one absorber to the nucleic acid to be detected, such that a change of the measured intensity of the emission light correlates with the presence of the nucleic acid to be detected;
wherein the attenuation of at least one of the emission light and the excitation light by the at least one absorber occurs independently of a quantum yield of the at least one dye, wherein the kit is capable of performing the method of claim 1.

* * * * *

```
                        SEQUENCE LISTING

<160> NUMBER OF SEQ ID NOS: 9

<210> SEQ ID NO 1
  <211> LENGTH: 35
  <212> TYPE: DNA
  <213> ORGANISM: Artificial squence
  <220> FEATURE:
  <223> OTHER INFORMATION: synthetic functional nucleic acid
  <220> FEATURE:
  <221> NAME/KEY: misc_feature
  <222> LOCATION: (1)..(1)
  <223> OTHER INFORMATION: 5'-Thiol-Adenine

<400> SEQUENCE: 1
naaaaaaaaa aaaaaaaaaa aaaaaaaaaa aaaaa                                    35

<210> SEQ ID NO 2
  <211> LENGTH: 25
  <212> TYPE: DNA
  <213> ORGANISM: Artificial Sequence
  <220> FEATURE:
  <223> OTHER INFORMATION: synthetic functional nucleic acid

<400> SEQUENCE: 2
agatggtatg tggaagttag attgg                                               25

<210> SEQ ID NO 3
  <211> LENGTH: 21
  <212> TYPE: DNA
  <213> ORGANISM: Artificial Sequence
  <220> FEATURE:
  <223> OTHER INFORMATION: synthetic functional nucleic acid

<400> SEQUENCE: 3
cctggaataa tgacgctatg a                                                   21

<210> SEQ ID NO 4
  <211> LENGTH: 25
  <212> TYPE: DNA
```

```
<213> ORGANISM: Artificial Sequence
<220> FEATURE:
<223> OTHER INFORMATION: synthetic functional nucleic acid

<400> SEQUENCE: 4
agatggtatg tggaagttag attgg                                          25

<210> SEQ ID NO 5
<211> LENGTH: 83
<212> TYPE: DNA
<213> ORGANISM: Artificial Sequence
<220> FEATURE:
<223> OTHER INFORMATION: synthetic functional nucleic acid

<400> SEQUENCE: 5
tcaatatgta tgctttggtc tttctgcatt cctggaataa tgacgctatg atcccaatct    60
aacttccaca taccatcttc ttt                                            83

<210> SEQ ID NO 6
<211> LENGTH: 35
<212> TYPE: DNA
<213> ORGANISM: Artificial Sequence
<220> FEATURE:
<223> OTHER INFORMATION: synthetic functional nucleic acid
<220> FEATURE:
<221> NAME/KEY: misc_feature
<222> LOCATION: (1)..(1)
<223> OTHER INFORMATION: 5'-Thiol-Adenine

<400> SEQUENCE: 6
naaaaaaaaa aaaaaaaaaa aaaaaaaaaa aaaaa                               35

<210> SEQ ID NO 7
<211> LENGTH: 20
<212> TYPE: DNA
<213> ORGANISM: Artificial Sequence
<220> FEATURE:
<223> OTHER INFORMATION: synthetic functional nucleic acid

<400> SEQUENCE: 7
gcagagcaag gactgataca                                                20

<210> SEQ ID NO 8
<211> LENGTH: 90
<212> TYPE: DNA
<213> ORGANISM: Artificial Sequence
<220> FEATURE:
<223> OTHER INFORMATION: synthetic functional nucleic acid

<400> SEQUENCE: 8
aatttgttcg catcaaacgg aaaatcacca tcatgtgtcc tactgattgc caagctgttg    60
gatattgtat cagtccttgc tctgcatgta                                     90

<210> SEQ ID NO 9
<211> LENGTH: 18
<212> TYPE: DNA
<213> ORGANISM: Artificial Sequence
<220> FEATURE:
<223> OTHER INFORMATION: synthetic functional nucleic acid

<400> SEQUENCE: 9
ccaatctaac ttcgacat                                                  18
```